United States Patent
Marks et al.

(10) Patent No.: US 7,671,202 B2
(45) Date of Patent: Mar. 2, 2010

(54) PERYLENE N-TYPE SEMICONDUCTORS AND RELATED DEVICES

(75) Inventors: Tobin J. Marks, Evanston, IL (US); Michael R. Wasielewski, Glenview, IL (US); Antonio Facchetti, Chicago, IL (US); Michael J. Ahrens, Evanston, IL (US); Brooks A. Jones, Evanston, IL (US); Myung-Han Yoon, Evanston, IL (US)

(73) Assignee: Northwestern University, Evanston, IL (US)

( * ) Notice: Subject to any disclaimer, the term of this patent is extended or adjusted under 35 U.S.C. 154(b) by 527 days.

(21) Appl. No.: 11/043,814

(22) Filed: Jan. 26, 2005

(65) Prior Publication Data

US 2005/0176970 A1  Aug. 11, 2005

Related U.S. Application Data

(60) Provisional application No. 60/539,133, filed on Jan. 26, 2004.

(51) Int. Cl.
*C07D 471/02* (2006.01)
*C07D 471/00* (2006.01)

(52) U.S. Cl. ............................... 546/37; 546/66
(58) Field of Classification Search ................. 546/37, 546/38, 66, 98, 99
See application file for complete search history.

(56) References Cited

U.S. PATENT DOCUMENTS

| | | | |
|---|---|---|---|
| 2,087,133 A | 7/1937 | Vollmann | |
| 4,378,302 A | 3/1983 | Aftergut et al. | 252/299.1 |
| 4,846,892 A | 7/1989 | Henning et al. | 106/478 |
| 5,405,962 A | 4/1995 | Muellen et al. | 546/27 |
| 5,472,494 A | 12/1995 | Hetzenegger et al. | 106/493 |
| 5,539,100 A | 7/1996 | Wasielewski et al. | |
| 5,677,417 A | 10/1997 | Muellen et al. | 528/310 |
| 5,808,073 A | 9/1998 | Böhm et al. | 546/39 |
| 5,908,583 A | 6/1999 | Havinga et al. | 252/500 |
| 5,986,099 A | 11/1999 | Müllen et al. | 546/26 |
| 6,063,181 A | 5/2000 | Bohm et al. | 106/493 |
| 6,084,099 A | 7/2000 | Hackmann et al. | 546/37 |
| 6,099,636 A | 8/2000 | Henning et al. | 106/493 |
| 6,124,458 A | 9/2000 | Müellen et al. | 546/38 |
| 6,143,905 A | 11/2000 | Bohm et al. | 549/232 |
| 6,165,661 A | 12/2000 | Hsiao et al. | |
| 6,184,378 B1 | 2/2001 | Bohm et al. | 546/37 |
| 6,252,245 B1 | 6/2001 | Katz et al. | 257/40 |
| 6,287,738 B1 | 9/2001 | Duff et al. | |
| 6,326,494 B1 | 12/2001 | Bohm et al. | 546/37 |
| 6,348,595 B1 | 2/2002 | Hendi | |
| 6,486,319 B1 | 11/2002 | Böhm et al. | 546/38 |
| 6,533,857 B1 | 3/2003 | Schmid et al. | 106/403 |
| 6,585,914 B2 | 7/2003 | Marks et al. | 252/500 |
| 6,608,323 B2 | 8/2003 | Marks et al. | 257/40 |
| 6,656,651 B1 | 12/2003 | Bender et al. | |
| 6,727,318 B1 | 4/2004 | Mathauer et al. | 524/801 |
| 6,784,301 B2 | 8/2004 | Hackmann et al. | 549/232 |
| 6,806,368 B2 | 10/2004 | Wurthner et al. | 546/37 |
| 6,878,825 B2 | 4/2005 | Krieger et al. | 546/28 |
| 6,890,377 B2 | 5/2005 | Böhm et al. | 106/31.47 |
| 6,916,928 B2 | 7/2005 | Becker et al. | 546/37 |
| 6,986,811 B2 | 1/2006 | Könemann et al. | 106/493 |
| 7,083,675 B2 | 8/2006 | Mizuguchi et al. | 106/498 |
| 7,105,046 B2 | 9/2006 | Mizuguchi et al. | 106/498 |
| 7,105,674 B2 | 9/2006 | Hackmann et al. | 546/37 |
| 7,326,956 B2 | 2/2008 | Shukla et al. | |
| 7,422,777 B2 | 9/2008 | Shukla et al. | |
| 2003/0181721 A1 | 9/2003 | Wurthner et al. | 546/37 |
| 2003/0219625 A1 | 11/2003 | Wolk et al. | 428/690 |
| 2004/0013959 A1 | 1/2004 | Bender et al. | |
| 2004/0023061 A1 | 2/2004 | Kathirgamanathan et al. | 428/690 |
| 2005/0075453 A1 | 4/2005 | Mathauer et al. | 524/801 |
| 2005/0092982 A1 | 5/2005 | Mullen et al. | 257/40 |
| 2005/0106415 A1 | 5/2005 | Jarikov et al. | 428/690 |
| 2005/0131220 A1 | 6/2005 | Dung et al. | 534/752 |
| 2005/0171252 A1 | 8/2005 | Schambony et al. | 524/90 |
| 2005/0222416 A1 | 10/2005 | Bohm et al. | 546/26 |
| 2005/0238974 A1 | 10/2005 | Sekiya et al. | |
| 2005/0251930 A1 | 11/2005 | Erk et al. | 8/512 |
| 2006/0058330 A1 | 3/2006 | Krieger et al. | 514/279 |
| 2006/0075585 A1 | 4/2006 | Krieger et al. | 8/642 |
| 2006/0131564 A1 | 6/2006 | Shukla et al. | 257/40 |
| 2006/0134823 A1 | 6/2006 | Shukla et al. | 438/99 |
| 2006/0141287 A1 | 6/2006 | Klubek et al. | 428/690 |
| 2006/0210898 A1 | 9/2006 | Jubran | |
| 2006/0229385 A1 | 10/2006 | Boehm | 523/161 |

(Continued)

FOREIGN PATENT DOCUMENTS

DE   2951349   7/1981

(Continued)

OTHER PUBLICATIONS

Ahrens,.M. et al.: Cyanated Perylene-3,4-dicarboximides and Perylene-3,4:9, 10-bis(dicarboximide), Chem. Mater. vol. 15, pp. 2684-2686, 2003.*
Facchetti et al., "Tuning the Semiconducting Properties of Sexithiophene by a, w-Substitution—α,ω-Diperfluorohexylsexithiophene: the First n-Type Sexithiophene for Thin-film Transistors," *Angew. Chem. Int. Ed.*, 2000: 39, 4547-4551.
Facchetti et al., "n-Type Building Blocks for Organic Electronics: a Homologous Family of Fluorocarbon-substituted Thiophene Oligomers with High Carrier Mobility,"*Adv. Mater.*, 2003: 15, 33-38.
Facchetti et al, "Building Blocks for n-Type Organic Electronics.

(Continued)

*Primary Examiner*—Charanjit S Aulakh
(74) *Attorney, Agent, or Firm*—K&L Gates LLP

(57) ABSTRACT

Mono- and diimide perylene and naphthalene compounds, N- and core-substituted with electron-withdrawing groups, for use in the fabrication of various device structures.

29 Claims, 8 Drawing Sheets

U.S. PATENT DOCUMENTS

| | | | |
|---|---|---|---|
| 2006/0237712 A1 | 10/2006 | Shukla et al. | |
| 2007/0026332 A1 | 2/2007 | Ferrar et al. | |
| 2007/0096084 A1 | 5/2007 | Shukla et al. | |
| 2007/0116895 A1 | 5/2007 | Shukla et al. | |
| 2008/0021220 A1 | 1/2008 | Marks et al. | 546/68 |
| 2008/0135833 A1 | 6/2008 | Shukla et al. | |
| 2008/0161569 A1 | 7/2008 | Dung et al. | |
| 2008/0167435 A1 | 7/2008 | Marks et al. | 526/259 |
| 2008/0177073 A1 | 7/2008 | Facchetti et al. | 546/34 |
| 2008/0185555 A1 | 8/2008 | Facchetti et al. | 252/182.3 |
| 2008/0185577 A1 | 8/2008 | Facchetti et al. | 257/40 |
| 2008/0249309 A1 | 10/2008 | Facchetti et al. | |

FOREIGN PATENT DOCUMENTS

| | | | |
|---|---|---|---|
| DE | 3434059 | | 3/1985 |
| DE | 3620332 | | 12/1987 |
| DE | 3703131 | | 8/1988 |
| DE | 4018830 | | 12/1991 |
| DE | 4338784 | A1 * | 5/1995 |
| DE | 4440242 | | 5/1996 |
| DE | 19501737 | | 7/1996 |
| DE | 19547210 | | 6/1997 |
| DE | 19622673 | | 12/1997 |
| DE | 19651712 | A1 * | 6/1998 |
| DE | 19709008 | | 9/1998 |
| DE | 10038672 | A1 * | 5/2002 |
| DE | 10148172 | | 4/2003 |
| EP | 1 526 496 | | 5/1968 |
| EP | 0 031 065 | | 10/1983 |
| EP | 0 217 256 | | 4/1987 |
| EP | 0 422 535 | | 4/1991 |
| EP | 0 826 740 | | 3/1998 |
| EP | 0 861 878 | | 9/1998 |
| EP | 0 896 964 | | 2/1999 |
| EP | 0 990 951 | | 4/2000 |
| EP | 1 172 700 | | 1/2002 |
| EP | 1 671 674 | | 6/2006 |
| FR | 2 237 922 | | 2/1975 |
| JP | 05-025174 | | 2/1993 |
| JP | 5-27459 | * | 2/1993 |
| JP | 11-119455 | | 4/1999 |
| JP | 2002-302674 | | 10/2002 |
| JP | 2003-327587 | | 11/2003 |
| JP | 2004-093801 | | 3/2004 |
| JP | 2004-093802 | | 3/2004 |
| JP | 2004-152815 | | 5/2004 |
| JP | 2005-154409 | | 6/2005 |
| JP | 2005-189765 | | 7/2005 |
| JP | 2005-209887 | | 8/2005 |
| JP | 2006-028027 | | 2/2006 |
| WO | 1990/01480 | | 2/1990 |
| WO | 1996/22332 | | 7/1996 |
| WO | 1997/022607 | | 6/1997 |
| WO | 1997/022608 | | 6/1997 |
| WO | 1997/26301 | | 7/1997 |
| WO | 1998/32799 | | 7/1998 |
| WO | 1998/32802 | | 7/1998 |
| WO | 1998/49164 | | 11/1998 |
| WO | 2000/69829 | | 11/2000 |
| WO | WO 02/14414 | * | 2/2002 |
| WO | 2003/091345 | | 11/2003 |
| WO | 2003/104232 | | 12/2003 |
| WO | 2004/029028 | | 4/2004 |
| WO | 2005/047265 | | 5/2005 |
| WO | 2005/070894 | | 8/2005 |
| WO | 2005/070895 | | 8/2005 |
| WO | 2005/078023 | | 8/2005 |
| WO | 2005/092901 | | 10/2005 |
| WO | 2006/021307 | | 3/2006 |
| WO | 2006/037539 | | 4/2006 |
| WO | 2006/050860 | | 5/2006 |
| WO | 2006/093965 | | 9/2006 |
| WO | 2006/115714 | | 11/2006 |
| WO | 2007/074137 | | 7/2007 |
| WO | 2007/093643 | | 8/2007 |
| WO | 2008/091670 | | 7/2008 |

OTHER PUBLICATIONS

Regiochemically Modulated Inversion of Majority Carrier Sign in Perfluoroarene-Modified Polythiophene Conductors," *Angew. Chem. Int. Ed.*, 2003: 42, 3900-3903.

Jones et al., "Tuning Orbital Energetics in Arylene Diimide Semiconductors. Materials Design for Ambient Stability of n-Type Charge Transport," *J. Am. Chem. Soc.*, 2007: 129, 15259-15278.

Müller et al., "Facile synthetic approach to novel core-extended perylene carboximide dyes," *Chem. Commun.*, (2005) 4045-4046.

Blaszczyk et al., "Synthesis, Structure, and Optical Properties of Terminally Sulfur-Functionalized Core-Substituted Naphthalene-Bisimide Dyes," *Helvetica Chimica Acta*, 89:1986-2005 (2006).

Désilets et al., "Design and synthesis of near-infrared absorbing pigments. II. Structure determination of aceanthrene green and derivatives," *Can. J. Chem.*, 73:325-335 (1995).

Dobrawa et al., "Fluorescent Supramolecular Polymers: Metal Directed Self-Assembly of Perylene Bismide Building Blocks," *Macromolecules*, 38:1315-1325 (2005).

Fan et al.,"1,6-Disubstituted perylene bisimides: concise synthesis and characterization as near-infrared fluorescent dyes," *Tetrahedron Letters*, 46:4443-4447 (2005).

Langhals et al., "Naphthalene Amidine Imide Dyes by Transamination of Naphthalene Bisimides," *Chem. Eur. J.*, 12:2815-2824 (2006).

Liu et al., "Assembly and Characterization of Novel Hydrogen-Bond-Induced Nanoscale Rods," *J. Org. Chem.*, 69(26):9049-9054 (2004).

Prodi et al., "Wavelength-Dependent Electron and Energy Transfer Pathways in a Side-to-Face Ruthenium Porphyrin/Perylene Bisimide Assembly," *J. Am. Chem. Soc.*, 127:1454-1462 (2005).

Qian et al., "S-heterocyclic annelated perylene bisimide: synthesis and co-crystal with pyrene," *Chem. Commun.*, 4587-4589 (2006).

Röger et al., "Efficient Energy Transfer from Peripheral Chromophores to the Self-Assembled Zinc Chlorin Rod Antenna: A Bioinspired Light-Harvesting System to Bridge the Green Gap," *J. Am. Chem. Soc.*, 128:6542-6543 (2006).

Shibano et al., "Synthesis and Photophysical Properties of Electron-Rich Perylenediimide-Fullerene Dyad," *Org. Lett.*, 8(20):4425-4428 (2006).

Thalacker et al., "Synthesis and Optical and Redox Properties of Core-Substituted Naphthalene Diimide Dyes," *J. Org. Chem.*, 71(21):8098-8105 (2006).

van der Boom et al., "Charge Transport in Photofunctional Nanoparticles Self-Assembled from Zinc 5, 10, 15, 20-Tetrakis(perylenediimide)porphyrin Building Blocks," *J. Am. Chem. Soc.*, 124(32):9582-9590 (2002).

Würthner et al., "Core-Substituted Naphthalene Bisimides: New Fluorophors with Tunable Emission Wavelength for FRET Studies," *Chem. Eur. J.*, 8(20):4742-4750 (2002).

Wërthner et al., "Preparation and Characterization of Regioisomerically Pure 1,7-Disubstituted Perylene Bisimide Dyes," *J. Org. Chem.*, 69:7933-7939 (2004).

Xiao et al., "Dyads and Triads Containing Perylenetetracarboxylic Diimide and Porphyrin: Efficient Photoinduced Electron Transfer Elicited via Both Excited Singlet States," *J. Phys. Chem.*, 109(8):3658-3667 (2005).

Baier et al., "Intermolecular energy transfer after vibrational excitation of a perylene dye in solution, in polymer binder, and in a side-chain copolymer," J. Chem. Phys., 114: 6739-6743 (2001).

Buncel et al.,"Synthesis and characterization of [3,3]- and [3,4]-perinophane," *Tetrahedron Letters*, 42:3559-3562 (2001).

Chen et al., "Oligothiophene-Functionalized Perylene Bisimide System: Synthesis, Characterization, and Electrochemical Polymerization Properties," *Chem. Mater.*, 17:2208-2215 (2005).

Database Caplus [Online] Chemical Abstracts Service, Columbus, Ohio, US; May 12, 1984 (May 12, 1984), XP002493285 retrieved from STN Database accession No. 1984:34294 abstract.

Database WPI Thomson Scientific, London, GB; AN 1983-750663 XP002493286 and JP 58 124790 A (Matsushita Electric Ind. Co. Ltd.) Jul. 25, 1983 (Jul. 25, 1983) abstract.

Giaimo et al, "Excited-State Symmetry Breaking in Cofacial and Linear Dimers of a Green Perylenediimide Chlorophyll Analogue Leading to Ultrafast Charge Separation," *J. Am. Chem. Soc.*, 124:8530-8531 (2002).

Holman et al.,"Studying and Switching Electron Transfer: From the Ensemble to the Single Molecule," *J. Am. Chem. Soc.*, 126: 16126-16133 (2004).

Huttner et al., "N-type organic field effect transistors from perylene bisimide block copolymers and homopolymers," *Appl. Phys. Lett.*, 92: 093302 (2008).

Jones et al., "Cyanonaphthalene Diimide Semiconductors for Air-Stable, Flexible, and Optically Transparent n-Channel Field-Effect Transistors," *Chem. Mater.*, 19(11):2703-2705 (2007).

Jones et al, "High-Mobility Air-Stable n-Type Semiconductors with Processing Versatility: Dicyanoperylene-3,4:9, 10-bis(dicaboximides)," *Angew., Chem. Int. Ed.*, 43:6363-6366 (2004).

Kwan et al., "Electrochemistry of Langmuir-Blodgett and Self-Assembled Films Built from Oligoimides," *Langmuir*, 8:3003-3007 (1992).

Langhals et al., "Tangentially Coupled π Systems and their Through-Space Interaction - Trichromophoric Perylene Dyes," *J. Prakt. Chem.*, 338: 654-659 (1996).

Langhals et al., "Chiral Bifluorophoric Perylene Dyes with Unusually High CD Effects - A Simple Model for the Photosynthesis Reaction Center," *Leibigs Ann./Recueil.*, 1151-1153 (1997).

Lindner et al., "Nanostructures of N-type organic semiconductor in a p-type matrix via self-assembly of block copolymers," *Macromolecules*, 37:8832-8835 (2004).

Lindner et al., "Charge Separation at Self-Assembled Nanostructured Bulk Interface in Block Copolymers," *Angew. Chem. Int. Ed.*, 45:3364-3368 (2006).

Lukas et al., "Femtosecond Optical Switching of Electron Transport Direction in Branched Donor-Acceptor Arrays," *J. Phys. Chem. B*, 104: 931-940 (2000).

Lukas et al., "Biomimetic Electron Transfer Using Low Energy Excited States: A Green Perylene-Based Analogue of Chloroophyll a," *J. Phys. Chem. B*, 106: 1299-1306 (2002).

Martyushina et al., "Searches for Nondepolarizing Short-Action Myorelaxants," *Pharm. Chem.*, 1982: 16(7), 801-806 (English translation pp. 524-530).

Morris et al., "Synthesis of Extended Linear Aromatics Using Tandem Diels-Alder Aromatization Reactions," *J. Org. Chem.* 59:6484-6486 (1994).

Petit et al., "Synthesis of macromolecular substances comprising dye derivatives as monomeric unites. III. Synthesis and study of monomeric dihydroxy dyes," *Bulletin de la Societe Chimique de France*, 7-8:1591-1596 (1974).

Rodriguez-Llorente et al.,"Infrared and Raman spectra of thin solid films of 1,2-bis(propylimido perylene) ethane," *Spectrochimica Acta. Part A*, 55: 969-978 (1999).

Rodriguez-Llorente et at, "Vibrational spectra and thin solid films of a bi(propylperylenediimide)," *J. Mater. Chem.*, 8(10):2175-2176 (1998).

Rodriguez-Llorente et al., "Spectroscopic characterization of thin solid films of a bis(chlorobenzylimidoperyleneimido)octane derivative," *J. Mater. Chem.*, 8(3): 629-632 (1998).

Rohr et al., "Liquid crystalline coronene derivatives," *J. Mater. Chem.*, 11:1789-1799 (2001).

Shimizu et al., "Convergent Functional Groups. 15. Synthetic and Structural Studies of Large and Rigid Molecular Clefts," *J. Am. Chem. Soc.*, 116:5145-5149(1994).

Singh et al., "Soluble derivatives of perylene and naphthalene diimide for n-channel organic field-effect transistors," *Organic Electronics*, 7:480-489 (2006).

Tauber et al., "Electron Hopping in π-Stacked Covalent and Self-Assembled Perylene Diimides Observed by ENDOR Spectroscopy," *JACS Comm.*, 128: 1782-1783 (2006).

Thalacker et al.," Hydrogen bond directed self-assembly naphthalene bisimides with melamines in solution and at the graphite interface," *Org. Biomol. Chem.*, 3:414-422 (2005).

Tsoi et al., "Distributed Bilayer Photovoltaics Based on Nematic Liquid Crystal Polymer Networks," *Chem. Mater.*, 19:5475-5484 (2007).

\* cited by examiner tCN₂PDI            cCN₂PDI

Substrate at RT    Substrate at 90°C

Thin Film Grown on 90° C Substrate
d = 17.9 A (x-ray)
l = 22.0 A (MM calc.)
θ = 35.3 ° (to the surface normal)

Stability (TFT cycled $V_{DS}$= 50, $V_G$ = 0 ↔ 50V)
OFF-ON CYCLES

PERYLENE N-TYPE SEMICONDUCTORS AND RELATED DEVICES

This application claims priority benefit of U.S. application Ser. No. 60/539,133, filed Jan. 26, 2004, the entirety of which is incorporated herein by reference.

The United States Government has certain rights to this invention pursuant to Grant Nos. N00014-02-1-0909 and N00014-02-1-0381 from the Office of Naval Research, DARPA Grant No. MDA972-03-1-0023, and Grant No. DMR-0076097 (MRC) from the National Science Foundation, all to Northwestern University.

BACKGROUND OF THE INVENTION

Organic semiconductors based on molecular and polymeric materials have become a major part of the electronics industry in the last 25 years as a complement to the shortcomings of inorganic semiconductors. Most notably, organic semiconductors offer, with respect to current inorganic-based technology, greater ease in substrate compatibility, device processability, flexibility, large area coverage, and reduced cost; as well as facile tuning of the frontier molecular orbital energies by molecular design. A key device used in the electronic industry is the field-effect transistor (FET) based on inorganic electrodes, insulators, and semiconductors. FETs based on organic semiconductor (OFET) may find niche applications in low-performance memory elements as well as integrated optoelectronic devices, such as pixel drive and switching elements in active-matrix organic light-emitting diode (LED) displays.

The thin-film transistor (TFT), in which a thin film of the organic semiconductor is deposited on top of a dielectric with an underlying gate (G) electrode, is the simplest and most common semiconductor device configuration. Charge-injecting drain-source (D-S) electrodes providing the contacts are defined either on top of the organic film (top-configuration) or on the surface of the FET substrate prior to the deposition of the semiconductor (bottom-configuration). The current between S and D electrodes is low when no voltage is applied between G and D electrodes, and the device is in the so called 'off' state. When a voltage is applied to the gate, charges can be induced into the semiconductor at the interface with the dielectric layer. As a result, the D-S current increases due to the increased number of charge carriers, and this is called the 'on' state of a transistor. The key parameters in characterizing a FET are the field-effect mobility ($\mu$) which quantifies the average charge carrier drift velocity per unit electric field and the on/off ratio ($I_{on}$:$I_{off}$) defined as the D-S current ratio between the 'on' and 'off' states. For a high performance OFET, the field-effect mobility and on/off ratio should both be as high as possible.

Most of the OFETs operable in p-type accumulation mode, meaning that the semiconductor acts as a hole-transporting material. However, for the full development of the field of organic semiconductors, high-performing electron-transporting (n-type) materials are needed as well. For most practical applications, the mobility of the field-induced charges should, optimally, be >0.1–1 $cm^2$/Vs. To achieve high performance, the organic semiconductors should also meet or approach certain criteria relating to both the injection and current-carrying phenomena, in particular: (i) HOMO/LUMO energies of individual molecules (perturbed by their placement in a crystalline solid) at levels where holes/electrons may be added at accessible applied voltages, (ii) a crystal structure of the material with sufficient overlap of the frontier orbitals ($\pi$ stacking and edge-to-face contacts) for charge migration among neighboring molecules, (iii) a compound with minimal impurities as charge carrier traps, (iv) molecules (in particular the conjugated core axes) preferentially oriented with their long axes close to the FET substrate normal, as efficient charge transport occurs along the direction of intermolecular $\pi$-$\pi$ stacking, and (v) uniform coverage of the crystalline semiconductor domains between source and drain contacts, preferably with a film having preferably with a film exhibiting a single crystal-like morphology.

Among n-type organic semiconductors used in OFETs, the class of arene core diimides is one of the most investigated. The first report on a diimide-based FET was on a series of naphthalene tetracarboxylic diimides, followed by reports of perylene tetracarboxylic diimides. Over the years, chemical modification and tailoring of the imide position has resulted in the production and testing of a library of diimide-based materials. However, such compounds have been found generally to be unstable in air and have solubility characteristics less than satisfactory for efficient device fabrication.

SUMMARY OF THE INVENTION

In light of the foregoing, it is an object of the present invention to provide n-type semiconductor compounds and/or devices and relates methods for their use, thereby overcoming various deficiencies and shortcoming of the prior art, including those outlined above. It will be understood by those skilled in the art that one or more aspects of this invention can meet certain objectives, while one or more other aspects can meet certain other objectives. Each objective may not apply or apply equally, in all its respects, to every aspect of this invention. As such, the following objects can be viewed in the alternative with respect to any one aspect of this invention.

It is an object of this invention to provide one or more of the present polycyclic aromatic mono- and/or diimide compounds core-substituted with one or more electron-withdrawing moieties or groups, and/or the radical anions electrochemically generated therefrom.

It is another object of the present invention, in conjunction with the preceding, to provide such compounds with a range of available electron withdrawing N-substituted moieties, groups and/or substituents.

It is another object of this invention to incorporate any one or more of the present compounds into a range of device structures including but not limited to organic light-emitting diodes, field-effect transistors, and photovoltaic devices.

It is another object of the present invention to use compounds of the type described herein to enhance oxidative stability and/or lower reduction potential(s) of such compounds, s compared to unsubstituted polycyclic compounds of the prior art.

Other objects, features, benefits and advantages of the present invention will be apparent from this summary and descriptions of various embodiments, and will be readily apparent to those skilled in the art having knowledge of n-type semiconductor materials, related device structures, and use thereof. Such objects, features, benefits and advantages will be apparent from the above as taken into conjunction with the accompanying examples, data, figures and all reasonably inferences to be drawn therefrom, alone or with consideration of the references incorporated herein.

This invention relates to mono-and diimide perylene and naphthalene compounds functionalized at core and imide positions with varying moieties for improved solubility and radical anion stability, while maintaining a strong $\pi$-$\pi$ interactions. The choice of moiety or functional group can vary as described herein but can take into consideration three factors:

1) electron-withdrawing capability, 2) capability of attachment to the π-conjugated core, and/or 3) potential for increased solubility of the compound for solution processing. Such compounds and related methods can be employed to enhance associated device (e.g., OFET) performance.

As described below, electronegative or electron-withdrawing functionalities, such as cyano substituents and fluorinated moieties, when substituted (e.g., N- or core substituted) on highly conjugated naphthalene or perylene structures are shown to improve electron injection—presumably, but without limitation, by facilitating formation of charge carriers in the form of radical anions. To illustrate such effects, a representative series of cyano-substituted perylene imides—with low reduction potentials, high solubility, and interesting optical characteristics—was synthesized. In particular, such core functionalized perylene diimide derivatives demonstrate large chemical/thermal stability and strong π-π intermolecular interactions. Accordingly, these compounds and others of the sort described herein can be used in the fabrication of OFETs and related device structures.

Without limitation as to any one device structure or end-use application, the present invention can relate to n-type semiconductor compounds of a formula selected from

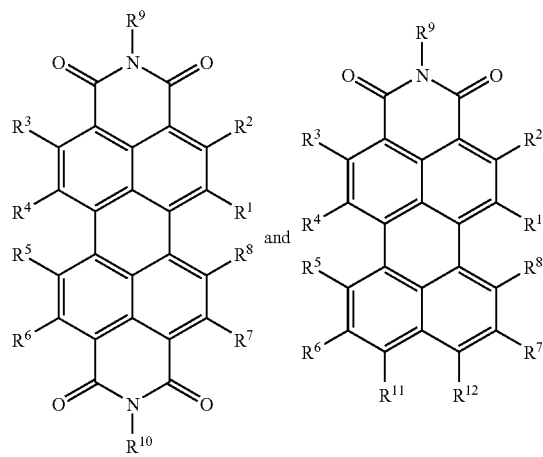

wherein each of $R^1$-$R^8$, $R^{11}$, and $R^{12}$ can be independently selected from H, an electron-withdrawing substituent and a moiety comprising such a substituent. Electron-withdrawing substituents include but are not limited to nitro, cyano, quaternary amino, sulfo, carbonyl, substituted carbonyl and carboxy substituents. Associated moieties can be but are not limited to alkyl, substituted alkyl, cycloalkyl, substituted cycloalkyl, aryl, substituted aryl, polycyclic aryl and substituted polycyclic aryl moieties. Without limitation, such moieties and associated electron-withdrawing substituents can be selected from $C_nF_{2n+1}$, $C_nH_2F_{2n-1}$ and C(O)R (e.g., R=H, alkyl, $C_nF_{2n+1}$ or $C_nH_2F_{2n-1}$) groups—as would be understood by those skilled in the art and made aware of this invention. At least one of $R^1$-$R^8$, $R^{11}$, and $R^{12}$ is selected from one of such substituents and/or associated moieties. $R^9$ and $R^{10}$ are independently selected from H, alkyl, substituted alkyl, cycloalkyl, substituted cycloalkyl, aryl, substituted aryl, polycyclic aryl and substituted polycyclic aryl moieties. Any such moiety can comprise one or more of the aforementioned electron-withdrawing substituents. For example, without limitation, certain substituted alkyl moieties can include $C_nH_{2n+1}$, $C_nF_{2n+1}$, $C_nH_2F_{2n-1}$ and the like. Further, one or more methylene (—$CH_2$—) or methene (—CH=) components of any such alkyl or aryl moiety can be substituted with a heteroatom (e.g., O or N) to provide the corresponding substituted moiety (e.g., ether, amine, polyether, polyamine and corresponding heteroaromatic moieties).

In certain other embodiments, at least one of $R^1$, $R^4$, $R^5$, $R^8$, $R^{11}$, and $R^{12}$ can be either an electron-withdrawing substituent or a moiety comprising such a substituent. In certain other embodiments, such electron-withdrawing substituents can be selected from fluorine and substituents having a Hammett $\sigma^+$ value $\leq 0.3$. Without limitation, at least one of $R^1$, $R^4$, $R^5$, $R^8$, $R^{11}$, and $R^{12}$ can be a cyano substituent. In certain other embodiments, as discussed more fully below, such cyanated compounds can be di- or tetra-substituted, as shown in the following representative structures.

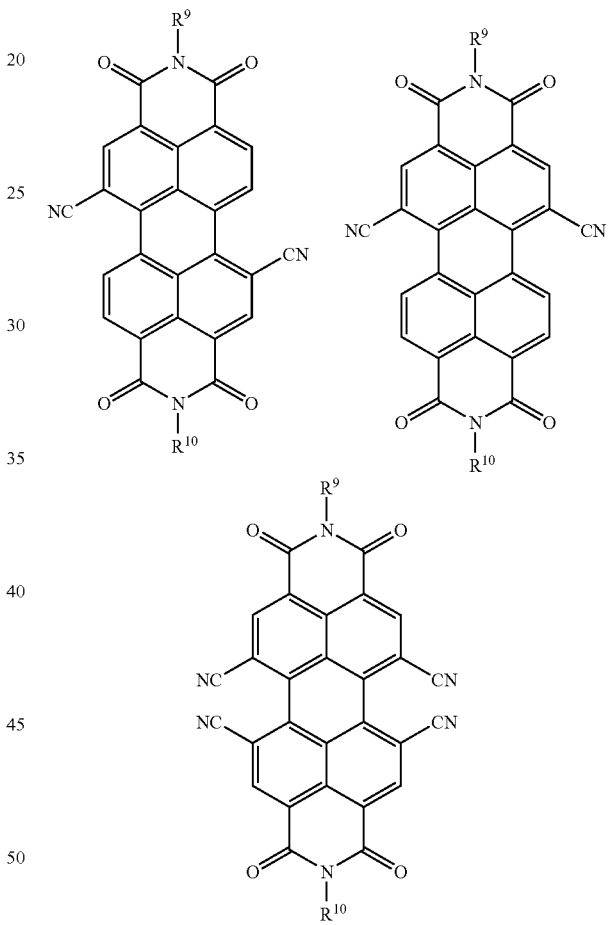

Regardless of core substitution, in certain embodiments, at least one of $R^9$ and $R^{10}$ can be selected, optionally, fluoro-substituted, regardless of any particular pattern or degree or core substitution.

Likewise, without regard to any particular end-use application, this invention can be directed to composites of the type incorporated into a range of device structures. Such a composite can comprise a suitable substrate; and a semiconductor component, with or without the presence of any additional functional layer, film or component therebetween. Such a semiconductor component can comprise a compound of a formula selected from

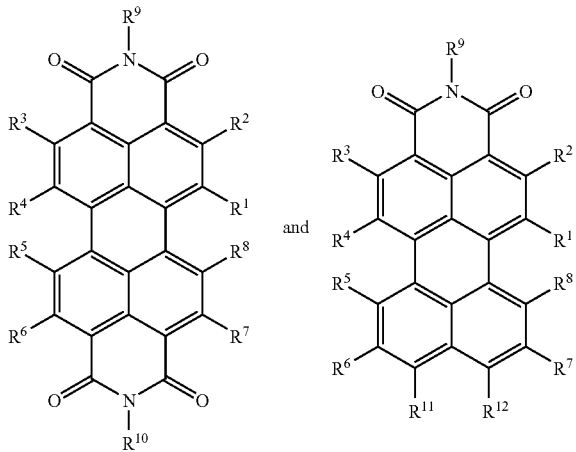

such compounds N- and core-substituted, as described above. In certain embodiments, such a composite can be incorporated into an OFET or another device structure. Regardless, core substitution can be used to enhance oxidative stability and/or to lower the reduction potential(s) of such a compound, as compared to unsubstituted perylene compounds of the prior art, and improve device performance.

In part, the present invention can also be directed to n-type semiconductor compounds of a formula selected from

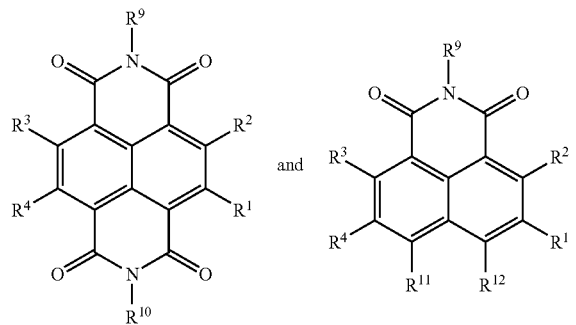

wherein $R^1$-$R^4$, $R^{11}$, and $R^{12}$ are independently selected from H and a cyano substituent, such that the compound is dicyano-substituted. $R^9$ and $R^{10}$ can be independently selected from H and moieties of the type described above in conjunction with various representative perylene compounds, such moieties as can be further substituted with one or more electron-withdrawing substituents of the sort described herein. Such compounds can be used as illustrated below for enhanced oxidative stability and/or to lower the reduction potential of such compounds as compared to unsubstituted naphthalene.

With respect to compounds, composites and/or methods of this invention, the compounds can suitably comprise, consist of, or consist essentially of any one or more of the aforementioned substituents and/or moieties. Each such compound or moiety/substituent thereof is compositionally distinguishable, characteristically contrasted and can be practiced in conjunction with the present invention separate and apart from one another. Accordingly, it should also be understood that the inventive compounds, composites and/or methods, as illustrated herein, can be practiced or utilized in the absence of any one particular compound, moiety and/or substituent— such compound, moiety and/or substituent which may or may not be specifically disclosed or referenced, the absence of which may not be specifically disclosed or referenced.

DETAILED DESCRIPTION OF CERTAIN EMBODIMENTS

Various features and benefits of this invention can be illustrated through the preparation and characterization of certain non-limiting n-type semiconductor compounds, such as the following mono-cyano (CN) di-cyano (CN$_2$) and tri-cyano (CN$_3$) mono-imide (MI) and diimide (DI) perylene compounds. Such compounds and their electrochemically-generated radical anions are shown to serve as stable, photochemical oxidants in a range of novel photonic and electronic films, materials and related device structures.

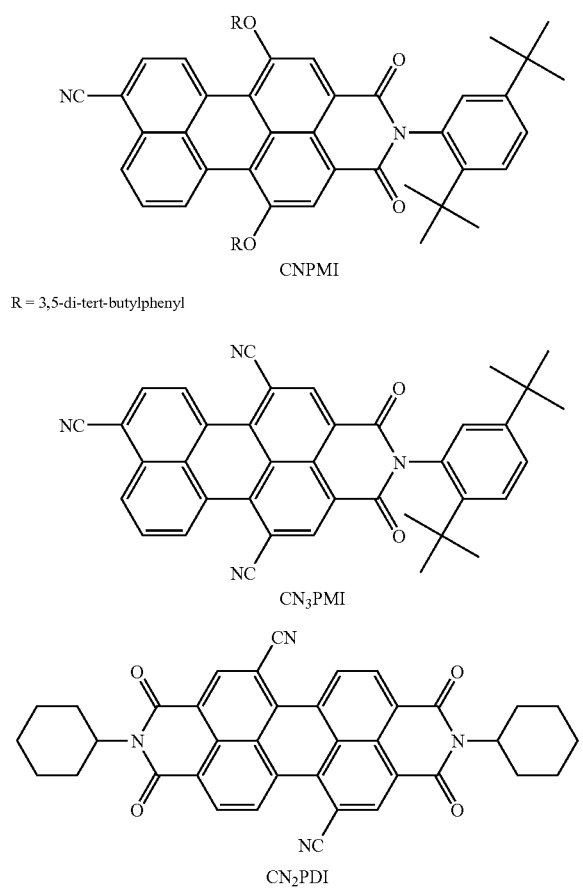

R = 3,5-di-tert-butylphenyl

CNPMI

CN$_3$PMI

CN$_2$PDI

The immediate precursors to such cyanoperylenes are the corresponding bromo derivatives: N,N-dicyclohexyl-1,7-dibromoperylene-3,4:9,10-bis(dicarboximide), N-(2,5-tert-butylphenyl)-9-bromoperylene-3,4-dicarboximide, and N-(2,5-tert-butylphenyl)-1,6,9-tribromoperylene-3,4-dicarboximide, which are readily synthesized in high yields by direct bromination of the parent hydrocarbons. Classical cyanation procedures using CuCN in refluxing DMF failed to produce the desired cyano compounds. In all three cases this procedure resulted in significant yields of debrominated products. Recently, Zn(CN)$_2$ or CuCN in the presence of a Pd(0) catalyst has been used to convert bromoarenes into cyanoarenes in excellent yields. The Zn(CN)$_2$ method was used to quantitatively convert all three bromoperylene derivatives to the corresponding cyano compounds, as described in the following examples.

TABLE 1

Photophysical and Electrochemical Properties

| compd | $\lambda_{abs}$ (nm) ∈ (M$^{-1}$ cm$^{-1}$) | $\lambda_{em}$ (nm) | $E_S$ (eV) | $\phi_F$ | $E^-_{1/2}$ (V) | $E^{2-}_{1/2}$ (V) |
|---|---|---|---|---|---|---|
| CN$_2$PDI | 530 47000 | 545 | 2.30 | 1.0 | −0.07[a] | −0.40[a] |
| CNPMI | 515 61000 | 541 | 2.35 | 0.91 | −0.73[b] | −1.14[b] |
| CN$_3$PMI | 522 60000 | 554 | 2.30 | 0.83 | −0.19[a] | −0.72[a] |

[a]Butyronitrile + 0.1 M Bu$_4$NClO$_4$.
[b]Butyronitrile + 0.1 M Bu$_4$NPF$_6$.
Electrochemical potentials vs SCE absorption spectroscopy, even when they are in the presence of other perylene derivatives.

Figure 1:
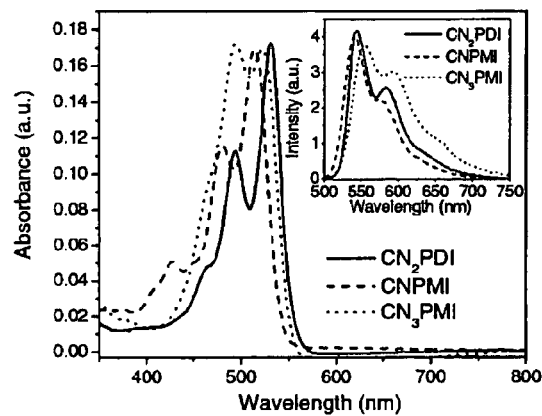
FIG. 1. Electronic absorption and fluorescence (inset) spectra of the indicated compounds in toluene. Fluorescence spectra were obtained following excitation at 480-490 nm.

The ground-state absorption and emission spectra of the neutral molecules in toluene are shown in FIG. 1. The intense absorbance maxima for each of these chromophores are near 500 nm and are only slightly shifted in wavelength relative to those of unsubstituted PMI (512 nm) and PDI (526 nm). In addition to the usual vibronic progression present in each of these rigid aromatic molecules, the spectrum of CNPMI shows an additional band at 420 nm, which is typical of 1,6-bisphenoxylated PMI derivatives. The 420-nm band partially obscures the second vibronic band of CNPMI at 450 nm. The cyanated derivatives all fluoresce with quantum yields $\phi_F$>0.8, determined relative to rhodamine 640 (Table 1). The absorption and emission features of these molecules are not solvatochromic, which coupled with the high fluorescence quantum yields suggest that their lowest excited singlet states possess little or no charge-transfer character. The energies of the lowest excited singlet states, $E_S$, were estimated by averaging the energies of their absorption and emission maxima, $\lambda_{abs}$ and $\lambda_{kcm}$, respectively.

Cyclic voltammetry on the cyanated derivatives shows that the one-electron reduction potentials ($E^-_{1/2}$ and $E^{2-}_{1/2}$) of each molecule are more positive than those of the unsubstituted analogues (PMI: $E^-_{1/2}$=−0.96, $E^{2-}_{1/2}$=−1.55 V; PDI: $E^-_{1/2}$=−0.43 V, $E^{2-}_{1/2}$=−0.70 V, all vs SCE)[13] (Table 1), CN$_2$PDI and CN$_3$PMI show exceptionally large positive shifts in redox potential. Spectroelectrochemical measurements yield the electronic absorption spectra of the radial anions of CNPMI, CN$_3$-PMI, and CN$_2$PDI and the dianion of CN$_2$PDI.

Figure 2:
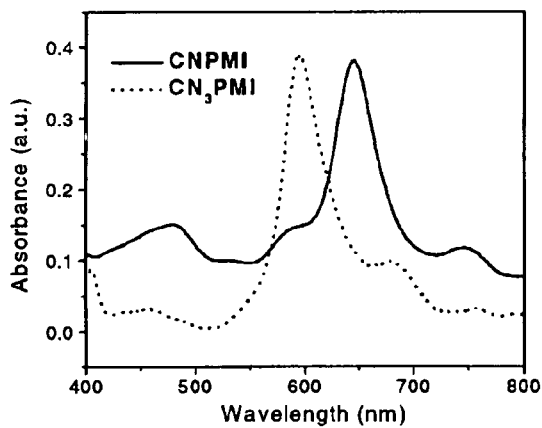
FIG. 2. Electronic absorption spectra of CNPMI and $CN_3PMI$ in butyronitrile containing 0.1 M $Bu_4NPF_6$ and 0.1 M $Bu_4NClO_4$, respectively, following controlled potential electrolysis at −0.9 and −0.3 V vs SCE, respectively.

The electronic absorption spectra of CNPMI$^-$ and CN$_3$PMI$^-$ in butyronitrile (FIG. 2) show that the absorption characteristics of the neutral molecules are replaced by new bands in the visible spectrum upon reversible electrochemical reduction of the chromophore to its radical anion. For example, the spectrum of CNPMI$^-$ is characterized by an intense absorption band at 644 nm, with minor bands at 480 and 735 nm. The spectrum of CN$_3$PMI$^-$ is similar to that of CNPMI$^-$ with an intense band at 595 nm and weaker bands at 458 and 680 nm. These bands can be compared to the corresponding intense absorption of PMI$^-$ at 588 nm.

Figure 3:
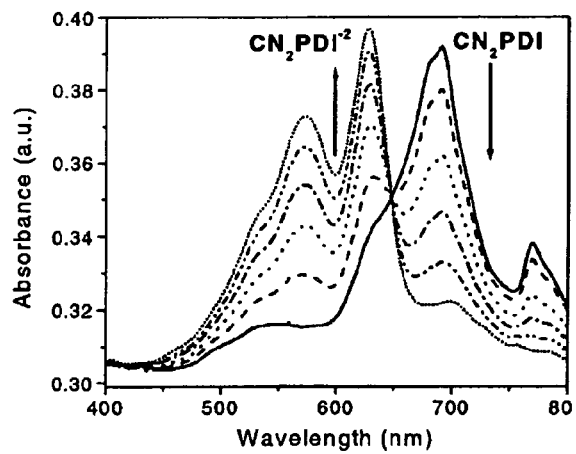
FIG. 3. Electronic absorption spectra of $CN_2PDI^-$ and $CN_2PDI^{2-}$ in DMF containing 0.1 M $Bu_4NClO_4$ following controlled potential electrolysis at −0.1 V vs SCE and at −0.6 V vs SCE, respectively.

FIG. 3 shows the electronic absorption spectra of CN$_2$PDI$^-$ and CN$_2$PDI$^{2-}$ obtained by controlled potential electrolysis of CN$_2$PDI, first at −0.1 V vs SCE and then at −0.6 V vs SCE. At the more negative potential, CN$_2$PDI$^-$ is cleanly and reversibly converted to CN$_2$PDI$^{2-}$ as noted by the isosbestic point at 650 nm. The intense absorption band of CN$_2$PDI$^{·-}$ at 691 nm is blue-shifted relative to that of PDI$^{·-}$ at 712 nm, while the corresponding absorption band of CN$_2$PDI$^{2-}$ at 628 nm is red-shifted relative to that of PDI$^{2-}$ at 570 nm. The relatively sharp band-width of these absorption features should make it possible to readily identify the presence of these radical anions and dianions at intermediates in electron-transfer reactions using transient absorption spectroscopy, even when they are in the presence of other perylene derivatives.

Figure 4:
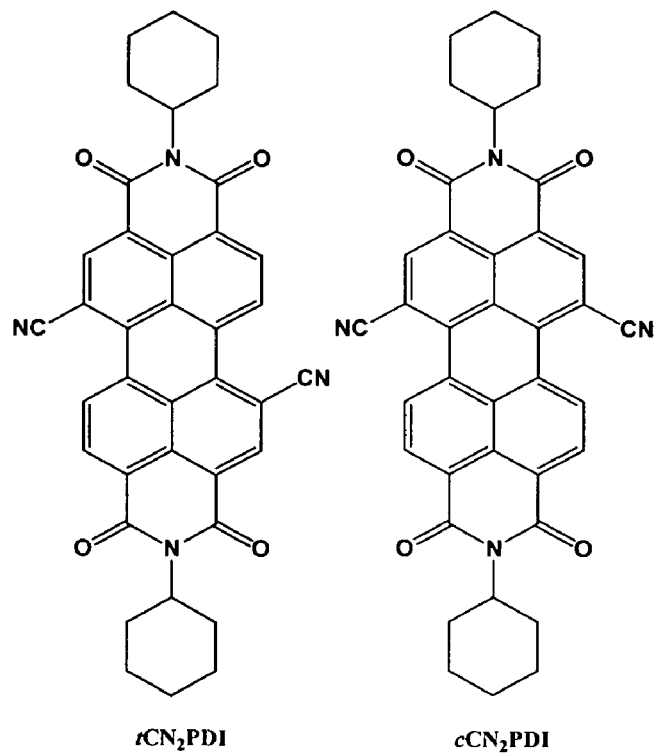
FIG. 4. Selected non-limiting dicyano compounds, $tCN_2PDI$ and $cCN_2PDI$.
Figure 5:
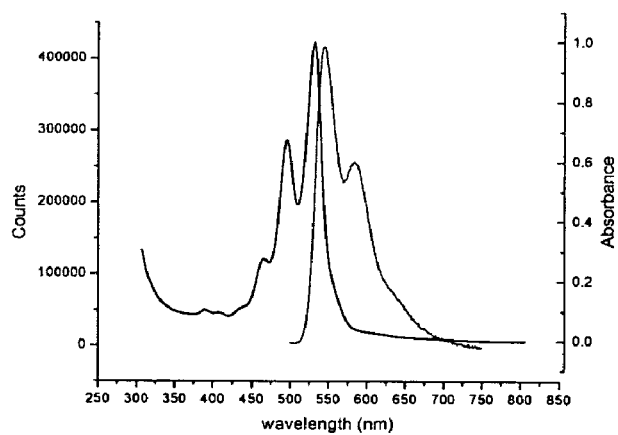
FIG. 5. UV-vis absorption and photoluminescence (PL) spectra of $tCN_2PDI$ and $cCN_2PDI$.

Under the synthesis preparation described, CN$_2$PDI (or, alternatively, designated PDI-CN$_2$, below) appears of be an approximately 50/50 mixture of tCN$_2$PDI and cCN$_2$PDI as shown by NMR. (FIG. 4) FIG. 5 shows optical spectra in a THF solution. By combining the electrochemical and optical data, absolute orbital energies can be estimated. LUMO energies can be determined from the first reduction potentials and HOMO energies considering the optical gap. The HOMO level is estimated to be at −7.10 eV and the LUMO level to be at −4.77 eV. These low lying MO energy levels allows for facile electron injection.

To demonstrates the effectiveness of CN$_2$PDI as a strong oxidant, the spectrum of this compound was monitored in the presence of an oxidizable species. For example, a 10$^{-5}$ M solution of CN$_2$PDI in dry DMF shows an absorption feature at 691 nm, indicating that about 15% of CN$_2$PDI is converted to CN$_2$DPI$^{·-}$ under ambient oxygenated conditions. Bubbling dry N$_2$ through the solution for 15 min produces a dramatic increase in the intensity of the CN$_2$PDI$^{·-}$ spectrum, indicating about 60% conversion to the radical anion. Since DMF typically contains a small amount of N,N-dimethylamine due to decomposition, it is possible that CN$_2$PDI oxidizes the amine. The aminium radical cation decomposes rapidly, yielding a proton, which is the counterion for the stable CN$_2$PDI$^{·-}$. This same effect can be observed in toluene, which is not oxidized by CN$_2$PDI, by adding a small amount of triethylamine to the toluene solution. While the first reduction potential of CN$_2$PDI is very similar to the well-known oxidant, chloranil (E[A/A$^-$]=0.02 V vs SCE), the radical anion and dianion of CN$_2$PDI, unlike the reduced chloranil species, are excellent chromophores themselves and are not susceptible to decomposition through irreversible protonation reactions. Moreover, both CN$_2$PDI and CN$_3$PMI are significantly easier to reduce than C$_{60}$ (E[A/A$^-$]=−0.38 V vs SCE), which is a typical electron acceptor in organic materials.

Figure 6:
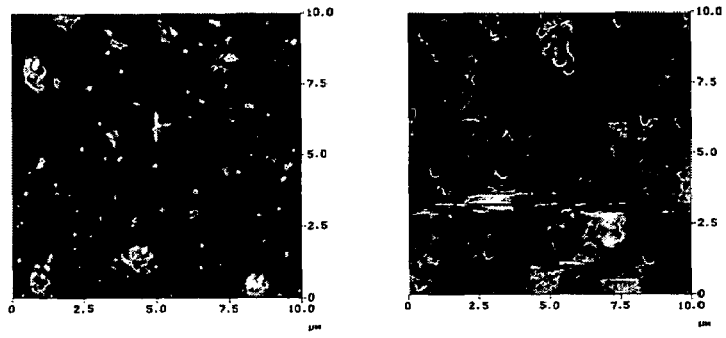
FIG. 6. X-ray diffraction data on a $CN_2$ PDI thin-film grown at room temperature and at a 90° C. substrate temperature.
Figure 7:
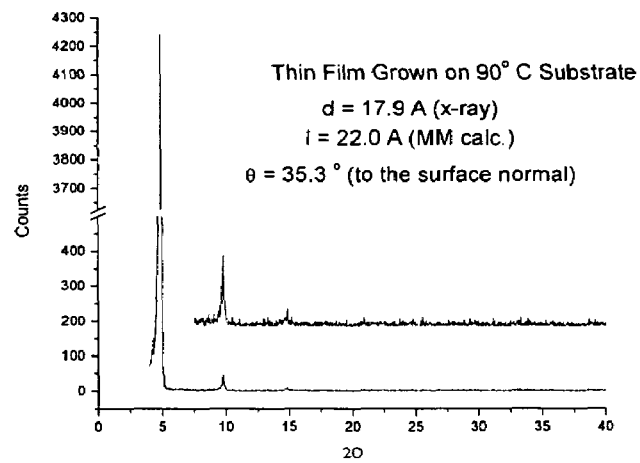
FIG. 7. AFM analysis of $CN_2PDI$ thin films grown at substrate temperatures of 25° C. and 90° C.
Figure 8:
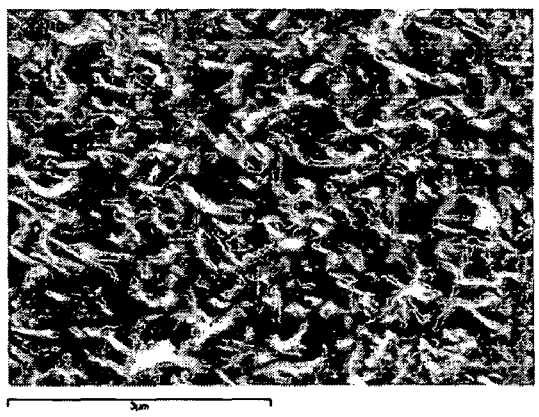
FIG. 8. SEM analysis of a $CN_2PDI$ thin film grown at 90° C. substrate temperature.

The film-forming properties of CN$_2$PDI were examined by X-ray diffraction, AFM, and SEM. (See, FIGS. 6-8.) Depending on chemical nature of the system, highly order or amorphous films can be produced as a function of deposition method (evaporation, spin-coating, casing), substrate temperature, and/or substrate pretreatment. For small molecules it is widely accepted that evaporation gives higher quality films; hence, analysis of the following films. X-ray diffraction reveals a d-spacing within the film of 17.9 Å. Based on a MM geometry optimization calculation, the length of these molecules is 22 Å. The tilt angle to the substrate normal is thus 35.3°. AFM data shows that films grown on a pretreated 90° C. substrate give the smoothest, most contiguous morphology.

A top-contact configuration was used to fabricate field effect transistor devices. The semiconductor mixture was vacuum-deposited on top of HMDS-treated Si/SiO$_2$ substrates kept at the temperature (T$_D$) of 25 and 90° C. The electrical measurements were performed under vacuum (~10$^{-4}$ Torr), N$_{2(g)}$, and in ambient atmosphere. The FET devices of this invention were fabricated as provided above and further described in U.S. Pat. No. 6,608,323, in particular Example 16 and FIG. 8 thereof, the entirety of which is incorporated herein by reference.

Figure 9:
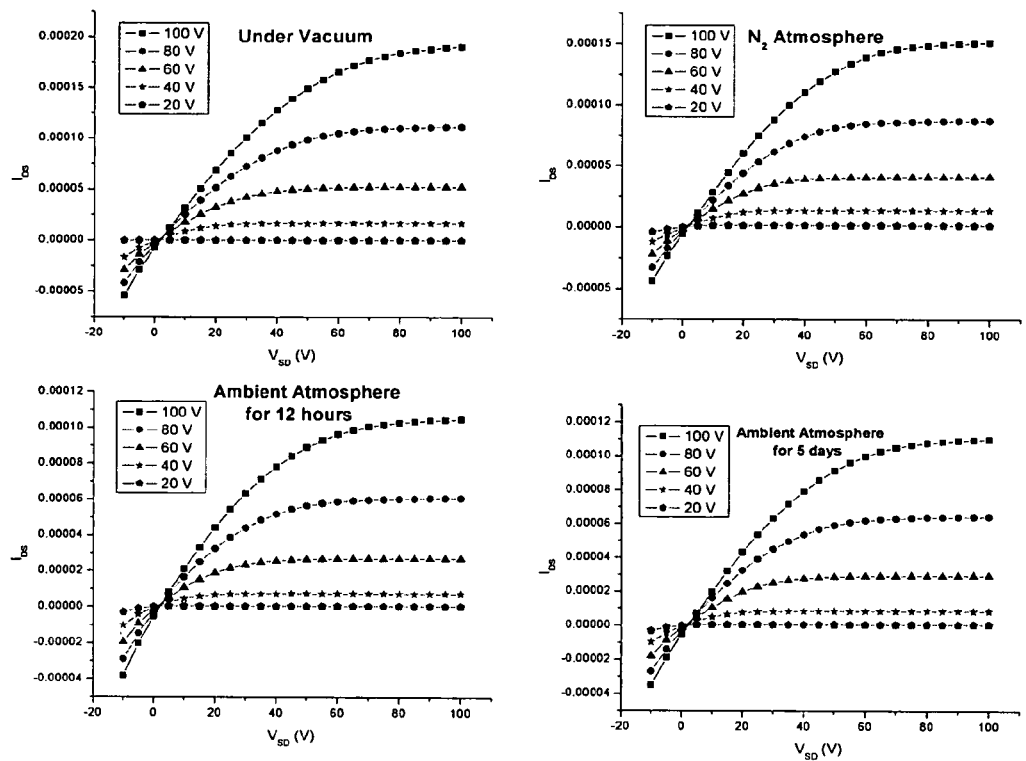
FIG. 9. FET current-voltage characteristics of $CN_2PDI$ under different positive gate-source biases in vacuum, $N_2$, in air after 12 hours, in air after 5 days.

FIG. 9 shows typical drain-source current/voltage plots of CN$_2$PDI operating at different gate bias in three atmospheric conditions. For purposes of comparison with other organic FETs, the mobilities were calculated by standard field effect transistor equations. In traditional metal-insulator-semiconductor FETs (MISFETs) there is typically a linear and saturated regime in the I$_{DS}$ vs D$_{DS}$ curves at different V$_G$. At large V$_{DS}$ the current saturates and is given by equation (1)

$$(I_{DS})_{sat}=(WC_i/2L)\mu(V_G-V_t)^2 \qquad (1)$$

where L and W are the device channel length and width, respectively, C$_i$ is the capacitance of the insulator (1×10$^{-8}$ F/cm$^2$ for 300 mm SiO$_2$). The mobility (μ) and the threshold voltage (V$_t$) can be calculated from the slope and intercept, respectively, of the linear section of the plot of V$_G$ versus (I$_{sd}$)$^{1/2}$ (at V$_{sd}$=−100 V). From these data n-type mobilities approaching 0.1 cm$^2$Vs, current on/off ratio of 10$^5$, and Vt of ~14 V were obtained in vacuum and N$_2$ atmospheres. Upon operation in air, mobilities of 0.05 cm$^2$/Vs were obtained. Optimization of film growth and materials purification will doubtless yield far higher mobilities.

The results with PDI-CN$_2$-derived OFETs (see below) suggested synthesis of another representative PDI derivative with additional electron-withdrawing substituents and greater volatility, e.g., N N-fluoroalkylsubstituted diimide designated PDI-FCN$_2$.

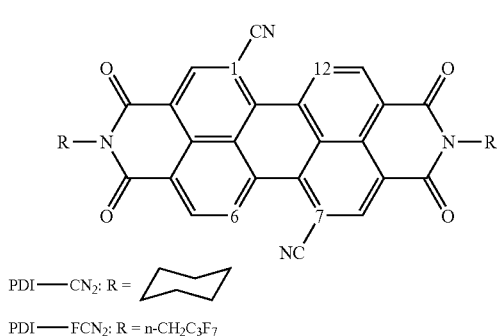

This compound was synthesized using modifications of literature core cyanation and N-fluoroalkylation procedures, and was characterized by heteronuclear NMR, mass spectrometry, optical absorption spectroscopy, photoluminescence, cyclic voltammetry, thermogravimetric analysis, and single-crystal x-ray diffraction. The electrochemical and optical data (Table 2) reveal further depression of the LUMO level vs. PDI/PDI-CN$_2$, while TGA indicates quantitative sublimation.

Figure 12:
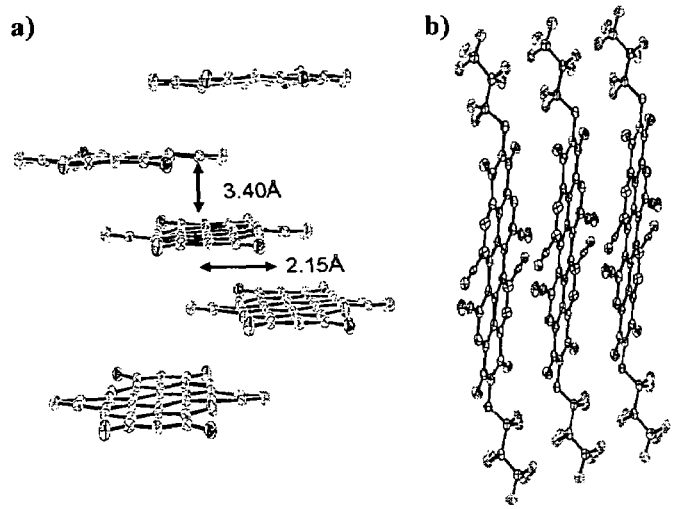
FIG. 12. Crystal structure of $PDI-FCN_2$ a) viewed along the unit cell diagonal, showing stacking relationships; fluoropropyl groups deleted for clarity; b) viewed along the ab face diagonal, showing the segregation of arene and fluoroalkyl groups. Note the statistical disorder of the cyano substituents.

As mentioned above, for both PDI materials, a 1:1 mixture of isomers (cyanated at the 1,7 or 1,6 positions) is indicated by NMR, however this characteristic is found to be inconsequential for spectroscopic, electric structural, and solid state charge transport properties (verified by measurements on small quantities of the pure 1,7 isomer). Single crystals of PDI-FCN$_2$ were grown by sublimation, and the crystal structure (FIG. 12) reveals a slightly twisted polycyclic core (torsional angle of ~5°) with slip-stacked face-to-face molecular packing and a minimum interplanar spacing of 3.40 Å. This motif appears to allow considerable intermolecular π-π overlap, resulting in good charge transport properties (see below). The positions of the disordered cyano substituents argues that this structural feature does not greatly affect packing.

TABLE 2

Electronic and OFET characteristics of perylene diimide derivatives.

| Compound | $\lambda_{abs}$ (nm)[a] | $\lambda_{em}$ (nm)[a] | $E_{(1)}(V)$[b] | $E_{(2)}(V)$[b] | $\mu$ (cm² V⁻¹ s⁻¹) | $I_{on}/I_{off}$ |
|---|---|---|---|---|---|---|
| PDI-CN$_2$ | 530 | 547 | −0.07 | −0.40 | 0.10 | 10⁵ |
| PDI-FCN$_2$ | 530 | 545 | +0.04 | −0.31 | 0.64 | 10⁴ |

[a]measured in THF (10⁻⁵/10⁻⁶ M)
[b]measured in 0.1 M TBAPF$_6$ solution in THF vs. S.C.E.

Figure 13:
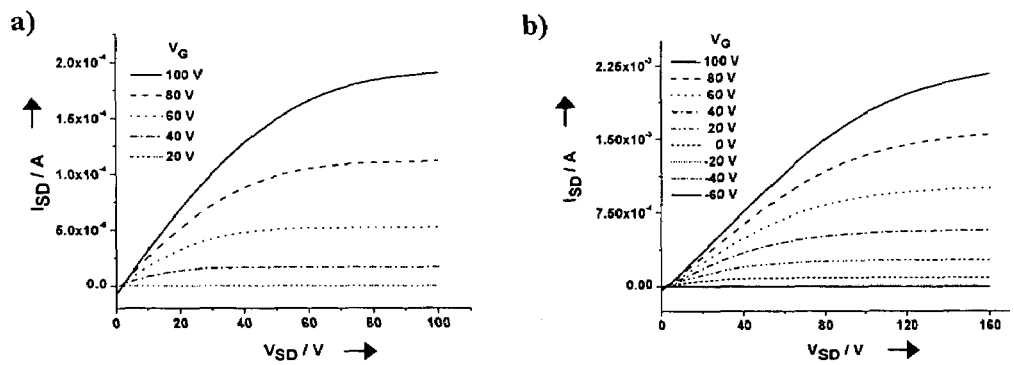
FIG. 13. a) I-V characteristics of $PDI-CN_2$ exhibiting a mobility of 0.10 $cm^2$ $V^{-1}$ $s^{-1}$ in ambient atmosphere b) I-V characteristics of a $PDI-FCN_2$ FET exhibiting a mobility of 0.64 $cm^2$ $V^{-1}$ $S^{-1}$ in ambient atmosphere.

For purpose of comparison, top-contact configuration OFETs were fabricated, as described below, with vapor-deposited PDI films (10⁻⁶ Torr, 0.2 Å/s growth), and mobilities determined in the saturation regime by standard procedures, [a] A. Facchetti, Y. Deng, A. Wang, Y. Koide, H. Sirringhaus, T. J. Marks, R. H. Friend, *Angew. Chem. Int. Ed. Engl.* 2000, 39, 4547; b) A. Facchetti, M. Mushrush, H. E. Katz, T. J. Marks, *Adv. Mater.* 2003, 15, 33; c) A. Facchetti, M.-H. Yoon, C. L. Stern, H. E. Katz, T. J. Marks, *Angew. Chem. Int. Ed. Engl.* 2003, 42, 3900.] The microstructures and mobilities of the vapor-deposited films are found to be sensitive to substrate temperature during growth. Due to the remarkable air-stability of these materials, all data presented here were acquired under ambient atmosphere (FIG. 13). PDI-CN$_2$-based OFETs display mobilities as high as 0.10 cm² V⁻¹ s⁻¹, threshold voltages of ~15 V, and $I_{on}/I_{off}$ (+100 V/0 V) ~10⁵, while PDI-FCN$_2$ devices exhibit mobilities as high as 0.64 cm² V⁻¹ s⁻¹, threshold voltages between −20 V and −30 V, and $I_{on}/I_{out}$ (+100 V/−60 V) as high as ~10⁴. Such mobilities are the highest values reported to date. Devices stored and tested under ambient conditions exhibit negligible degradation in mobility, threshold voltage, or $I_{on}/I_{off}$ on over the course of six months.

The microstructure of the vapor-deposited thin films was analyzed by XRD, AFM, and SEM, with XRD revealing d-spacings in highest-mobility devices of 17.9 Å and 20.3 Å for PDI-CN$_2$ and PDI-FCN$_2$, respectively. From a geometry-optimized, computed molecular length of 22.0 Å for PDI-CN$_2$ (Hyperchem (TM) 5.02, Hypercube, Inc., 1115 NW 4th Street, Gainesville, Fla. 32601, USA) and a crystallographically determined length of 22.8 Å for PDI-FCN$_2$, tilt angles relative to the substrate normal of 55° and 62°, respectively, are estimated. These results suggest favorable molecular orientations for source-to-drain electrode charge transport. AFM and SEM analysis of film morphology confirms polycrystalline topographies with ribbon-like grains (~400-800 nm long, ~100 nm wide). Such large-grained polycrystalline features should promote charge carrier mobility via efficient π-π intermolecular overlap and minimization of trap sites.

To investigate material versatility for applications, preliminary studies on bottom-contact OFETs and solution-cast films were performed. The bottom-contact devices display air-stable mobilities from 10⁻³ to 10⁻⁴ cm² V⁻¹ s⁻¹. PDI-FCN$_2$ transistors, like many fluorinated organic semiconductors, can be used with alkane thiol treatment of gold electrodes to better match surface energies at the metal/organic interface. Interestingly, PDI-CN$_2$ devices function without the aid of thiolated electrodes, retaining the ability of PDI to function on unmodified substrates. Top-contact devices fabricated from drip-cast films are also air-stable and exhibit mobilities of 10⁻³ to 10⁻⁵ cm² V⁻¹ s⁻¹. In contrast, solution casting of high-quality films of PDI derivatives not having core functionalization is difficult due to low solubility in common solvents.

One of the unique characteristics of such PDI systems is the presence of significant charge carrier densities at $V_G$=0 V. Thus, OFET threshold voltages for these materials are at $V_G$=−20 V to −30 V, with the absence of charge carriers then defining the 'off' state at −60 V, and classifying these devices as "always on" transistors. In some cases, the presence of charge carriers below $V_G$=0 V can be reversed by exposure to an oxidant, and for our devices, I$_2$ vapor increases the threshold voltage to >−5 V and decreases the $I_{SD}$ at $V_G$=0 V by up to an order of magnitude.

Of particular note is the air-stability of operation for PDI-FCN$_2$ and PDI-CN$_2$-based OFETs. It is thought that ambient stability in n-type organic semiconductors benefits from electron-withdrawing fluorinated substituents, which electronically stabilize the charge carriers as well as promote close packing via fluorocarbon self-segregation. Judging from the present redox potentials, the charge carriers are not initially expected to be thermodynamically stable with respect to O$_2$(g); however, the close-packed fluorine functionalities may help provide a kinetic barrier to oxidation. The strategic cyanation of PDI produces air-stable N-fluoroalkyl and N-alkyl materials, presumably reflecting carrier stabilization in the very low-lying LUMOs.

As shown above, this invention provides solution processable, polycyclic n-type organic semiconductors with high carrier mobility and air-stable OFET operation. Notable properties reflect a combination of electron withdrawing functionality at the core and/or imide positions. In particular, without limitation to any one theory or mode of operation, cyano substitution provides solubility for solution processing and stability of negatively charged polarons by lowering the LUMO to resist ambient oxidation. Likewise, electron-withdrawing N-functionalities are believed to aid polaron stability by further lowering the LUMO energies, but may also induce close molecular packing for increased intermolecular π-overlap and more efficient charge transport. With the rich chemistry for PDI functionalization available, various other derivatives—as would be known in the art by those aware of this invention—should prove informative in elucidating structure-function relationships in organic n-type electronics.

EXAMPLES OF THE INVENTION

The following non-limiting examples and data illustrate various aspects and features relating to the compounds, devices and/or methods of the present invention, including the use of various mono- and diimide, N- and core-substituted perylene and/or naphthalene compounds as n-type semiconductors and/or in conjunction with field effect transistor devices. Such substituted compounds are available through the synthetic methodologies described herein. While the utility of this invention is illustrated through the use of several such compounds, it will be understood by those skilled in the art that comparable results are obtainable with various other compounds, substituents, and/or substitution patterns, via precursor compounds either commercially available or as described in the literature and substituted as provided herein or using known reagents and straightforward variations of such synthetic techniques, as would be understood by those skilled in the art made aware of this invention.

General Information for characterization of CN$_2$PDI, CNPMI and CN$_3$PMI, ¹H nuclear magnetic resonance spectra were recorded on a Varian 400 MHz NMR spectrometer using TMS as an internal standard. Laser desorption mass spectra were obtained with a Perspective BioSystems time-of-flight MALDI mass spectrometer using a 2-hydroxy-1-naphthoic acid or dithranol matrix.

Spectroscopy. Absorption measurements were made on a Shimadazu (UV-1601) spectrophotometer using 0.2 cm path length cuvettes. Fluorescence quantum yields were obtained by integrating the fluorescence emission bands from each compound and rhodamine 640 using corrected spectra obtained on a PTI photon-counting spectrofluorimeter with 1 cm path length cuvettes. The absorbance of each sample was <0.1 at the excitation wavelength.

Electrochemistry. Electrochemical measurements were performed using a CH Instruments Model 660A electrochemical workstation. The solvents were butyronitrile containing 0.1 M tetra-n-butylammonium perchlorate or hexafluorophosphate electrolyte. A 1.0 mm diameter platinum disk electrode, platinum wire counter electrode, and Ag/Ag$_x$O reference electrode were employed. The ferrocene/ferrocinium (Fc/Fc$^3$, 0.52 vs. SCE) was used as an internal reference for all measurements.

Figure 10:
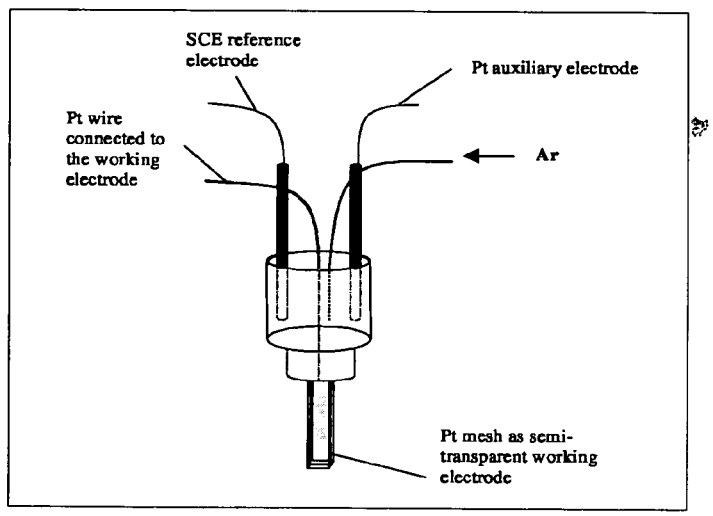
FIG. 10. Schematic illustration of a spectroelectrochemical cell of the type used herein to characterize compounds of this invention.

Spectroelectrochemistry. Spectroelectrochemical measurements were performed in the homemade quartz cell illustrated in FIG. 10. The cell consists of a 1 mm path length rectangular screw top spectrophotometric cuvette that is screwed into the bottom of a Teflon beaker. Platinum gauze, 100 mesh, woven from 0.07 mm diameter wire was used as a transparent working electrode. The electrode was placed in the 1 mm spectrophotometric cell and connected to the potentiostate (CH Instruments Model 660A) output by a platinum wire. The platinum wire counter and silver wire reference electrodes were placed in the Teflon reservoir, which held a solution of 0.1 M tetra-n-butylammonium perchlorate or hexafluorophosphate in butyronitrile. The electrochemical workstation controlled the potential of the working electrode, and a Shimadazu 1610A UV-VIS spectrometer obtained the absorption spectra of the redox species. All electrochemical measurements were carried out under a blanket of argon. A series of absorption spectra of the samples were taken until the potential induced spectral evolution was complete, which usually took 7 or 8 minutes.

Example 1

N,N-bis(cyclohexyl)-1,7-dicyano-perylene-3,4:9,10-bis(dicarboximide) (CN$_2$PDI). N,N-bis(cyclohexyl)-1,7-dibromo-perylene-3,4:9,10-bis(dicarboximide) 0.048 g, 0.07 mmol), zinc cyanide (0.065 g, 0.55 mmol), 1,1'-bis(diphenylphosphino)-ferrocene (0.005 g, 0.01 mmol) and tris (dibenzylideneacetone)-dipalladium(0) (0.010 g, 0.01 mmol) were combined in 4 ml p-dioxane and refluxed for 19 hours under a nitrogen atmosphere. The crude product was diluted with chloroform, filtered through Celite, and the solvent removed on a rotary evaporator. The crude product was chromatographed on a silica column using 98% DCM/2% acetone as the eluent to yield 0.041 g product CN$_2$PDI (theory 0.041 g, quantit). $^1$H NMR (CDCl$_3$): 9.692 (d, J=8.1 Hz, 2H), 8.934 (s, 2H), 8.888 (d, J=8.1 Hz, 2H), 5.025 (m, 2H), 2.533 (m, 4H), 1.931 (m, 4H), 1.755 (m, 6H), 1.504 (m, 4H), 1.329 (m, 2H). M.S.(EI): Calcd. for C$_{38}$H$_{28}$N$_4$O$_4$.604.2105, Found: 604.2108.

Example 2

N-(2,5-di-tert-butylphenyl)-9-cyano-1,6-bis(3,5-di-tert-butylphenoxy)perylene-3,4-dicarboximide (CNPMI). N-(2,5-di-tert-butylphenyl)-9-bromo-1,6-bis(3,5-di-tert-butylphenoxy)-perylene-3,4-dicarboximide (0.100 g, 0.10 mmol), zinc cyanide (0.047 g, 0.40 mmol), 1,1'bis(diphenylphosphino)-ferrocene (0.009 g, 0.02 mmol) and tris (dibenzylideneacetone)-dipalladium(0) (0.003 g, 0.003 mmol) were combined in 10 ml p-dioxane in a 25 ml round-bottom flask and heated to reflux for 36 hours under a N$_2$ atmosphere. Upon cooling to room temperature, the crude reaction mixture was diluted with chloroform, washed twice with water, and the solvent removed on a rotary evaporator. The crude product was flash chromatographed on a silica column using a 65% hexanes/35% chloroform mixture was the eluent to afford 0.094 g product (CNPMI) (theory 0.094 g, quantitative). $^1$H NMR (CDCl$_3$): 9.525 (d, J=8.7 Hz, 1H), 9.422 (d, J=8.2 Hz, 1H), 8.342 (d, J=7.4 Hz, 1H), 8.281 (s, 2H), 8.021 (d, J=8.2 Hz, 1H), 7.844 (t, J=8.1 Hz, 1H), 7.516 (d, J=8.6 Hz, 1H), 7.394 (d, J=8.7 Hz, 1H), 7.305 (s, 2H), 7.020 (s, 4H), 6.952 (s, 1H), 1.2–1.4 (s, 72H). M.S.(EI): Calcd. for C$_{65}$H$_{70}$N$_2$O$_4$: 942.5330, Found: 942.5320.

Example 3

N-(2,5-di-tert-butylphenyl)-1,6,9-tricyano-perylene-3,4-dicarboximide (CN$_3$PMI), N-(2,5-di-tert-butylphenyl)-1,6,9-tribromo-perylene-3,4-dicarboximide (0.082 g, 0.11 mmol), zinc cyanide (0.156 g, 1.33 mmol), 1,1'bis(diphenylphosphino)-ferrocene (0.009 g, 0.02 mmol) and tris (dibenzylideneacetone)-dipalladium(0) (0.004 g, 0.004 mmol) were added to 5 ml p-dioxane and heated to reflux for 16 hours under a N$_2$ atmosphere. The reaction mixture was diluted with methylene chloride, filtered through Celite, and the solvent removed on a rotary evaporator. The crude product was flash chromatographed on a silica column using methylene chloride as the eluent to give 0.062 g product CN$_3$PMI (theory 0.064 g, 97%). $^1$H NMR (CDC13): 9.603 (d, J=8.8 Hz, 1H), 9.532 (d, J=7.3 Hz, 1H), 9.048 (s, 2H), 8.638 (d, J=7.3 Hz, 1H), 8.248 (d, J=7.3 Hz, 1H), 8.096 (t, J=7.3 Hz, 1H), 7.608 (d, J=8.8 Hz, 1H), 7.495 (d, J=8.8 Hz, 1H), 6.967 (s, 1H), 1.328 (s, 9H), 1.283 (s, 9H). M.S. (EI): Calcd. for C$_{39}$H$_{28}$N$_4$O$_2$: 584.2207, Found: 584.2199.

Example 4

Figure 11:
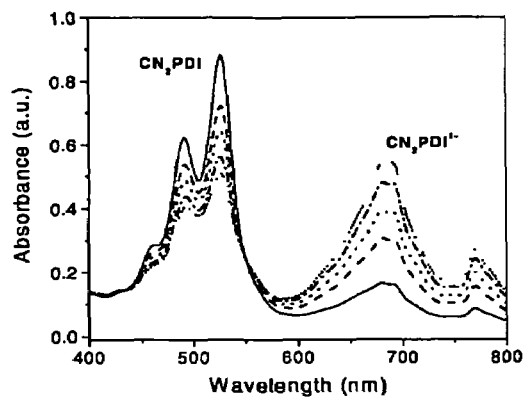
FIG. 11. $CN_2PDI$ ($10^{-5}$M) in dry DMF, ambient oxygen (solid line). Progressive increase over 15 min. of CN2PDI$^-$ spectrum while $N_2$ is bubbled into the cuvette (all other lines).

Oxidation Experiment. A 10$^{-5}$M solution of CN$_2$PDI in dry DMF under ambient oxygen conditions was placed in a cuvette and the spectrum was recorded by a Shimadzu 1601 uv-vis spectrophotometer. The solid line in FIG. 11 is that spectrum. Dry N$_2$ was bubbled into the cuvette over a period of 15 min. Spectra were recorded about every 3 min and are shown in the succession of traces that are dotted and dashed in FIG. 12. The most intense band at 691 nm occurs after the full 15 min of N$_2$ purging of the cuvette.

This invention shows that proper combination of core and imide substituents in arene diimides affect molecular and solid-state properties affording materials with unique properties. The results illustrate the relationship between molecular functionality, substituent electronic effects, and air-stability of the corresponding FET devices. The methods of synthesis and separation can be used to improve device performance. This class of arene diimides and/or specific compounds thereof are extremely promising materials for novel applications in electronics, photonics, and opto-electronics.

Pertaining to examples 5-12, $^1$H NMR spectra were recorded on a Varian 400 MHz NMR spectrometer using TMS as an internal standard. Laser desorption mass spectra were obtained with a Perspective BioSystems time-of-flight MALDI mass spectrometer using a dithranol matrix. Solvents and reagents were used as received. Flash and thin-layer chromatography was performed using Sorbent Technologies (Atlanta, Ga.) silica gel. All solvents were spectrophotometric grade. Toluene was purified by CuO and alumina columns (GlassContour).

Optical absorption measurements were made on a Shimadzu (UV-1601) spectrophotometer using 1.0 cm path length cuvettes. Fluorescence quantum yields were obtained by integrating the fluorescence emission bands from each compound and rhodamine 640 using corrected spectra obtained on a PTI photon-counting spectrofluorimeter with 1.0 cm path length cuvettes. The absorbance of each sample was <0.1 at the excitation wavelength.

Electrochemical measurements were performed using a CH Instruments Model 660A electrochemical workstation. The solvent was tetrahydrofuran containing 0.1 M tetra-n-butylammonium hexafluorophosphate electrolyte. A 1.0 mm diameter platinum disk electrode, platinum wire counter electrode, and Ag/Ag$_x$O reference electrode were employed. The ferrocene/ferrocinium (Fc/Fc$^+$, 0.52 vs. SCE) was used as an internal reference for all measurements.

Example 5

Synthesis of N,N'-bis(1H,1H-perfluorobutyl)-1,7-dibromo-perylene-3,4:9,10-bis(discarboximide). The reagent 1,7-dibromoperylene-3,4:9,10-tetracarboxydianhydride were prepared according to the literature. See, Ahrens, et al., *J. Am. Chem. Soc.*, 2004, 126, 8284-8236. The dibromo compound (0.920 g, 1.67 mmol) was combined with 20 mL 1-methyl-2-pyrrolidinone (NMP) and placed in a sonication bath for 20 min. Next, 2,2,3,3,4,4,4-heptafluorobutylamine (Fluorochemicals/SynQuest Labs) in 15 mL NMP was added, followed by addition of acetic acid (0.684 g, mmol). The reaction mixture was heated to 85-90° C. for 7 h under a N$_2$ atmosphere. The contents were cooled to room temperature, poured into 200 mL methanol, and placed in a –10° C. freezer overnight. The red precipitate was recovered by filtration, dried under a N$_2$ stream, and chromatographed on silica (chloroform) to afford (1) the bis(perfluoro) compound (1.196 g, 78%). $^1$H NMR (CDCl$_3$): δ 9.359 (d, J=8.15 Hz, 2H), δ 8.822 (s, 2H), δ 8.615 (d, J=8.15 Hz, 2H), δ 5.009 (m, 4H). M.S.: 912.51 (calcd. 909.88).

Example 6

Synthesis of N,N'-bis(1H-perfluorobutyl)-(1.7 & 1,6)-dicyano-perylene-3,4:9,10-bis(dicarboximide). N,N'-bis(1H,1H-perfluorobutyl)-1,7-dibromo-perylene-3,4:9,10-bis(dicarboximide) (1.196 g, 1.31 mmol), zinc cyanide (1.264 g, 10.8 mmol), 1,1'-bis(diphenylphosphino)ferrocene (0.119 g, 0.21 mmol), and tris(dibenzylideneacetone)-dipalladium(0) (0.041 g, 0.04 mmol) were combined in 20 mL p-dioxane and refluxed for 12 h under a N$_2$ atmosphere. The reaction mixture was then diluted with chloroform, filtered through Celite, and the solvent removed on a rotary evaporator. The resulting crude product was chromatographed on silica using 98% DCM/2% acetone as the eluent to yield (2) the dicyano compound (0.845 g, 80%). The product was further purified by high vacuum gradient temperature sublimations. $^1$H NMR (CDCl$_3$): δ 9.760 (d, J=6.20 Hz, 2H), δ 9.742 (d, J=6.22 Hz, 2H), δ 9.100 (s, 2H), δ 9.051 (s, 2H), δ 9.005 (d, J=8.19 Hz, 2H), δ 8.949 (d, J=8.17 Hz, 2H), δ 5.048 (m, 4H). M.S.: 804.42 (calcd. 804.05). Anal. Calcd. for C$_{34}$H$_{10}$F$_{14}$N$_4$O$_4$: C, 50.76, H, 1.25, N, 6.96. Found: C, 50.76, H, 1.34, N, 6.91.

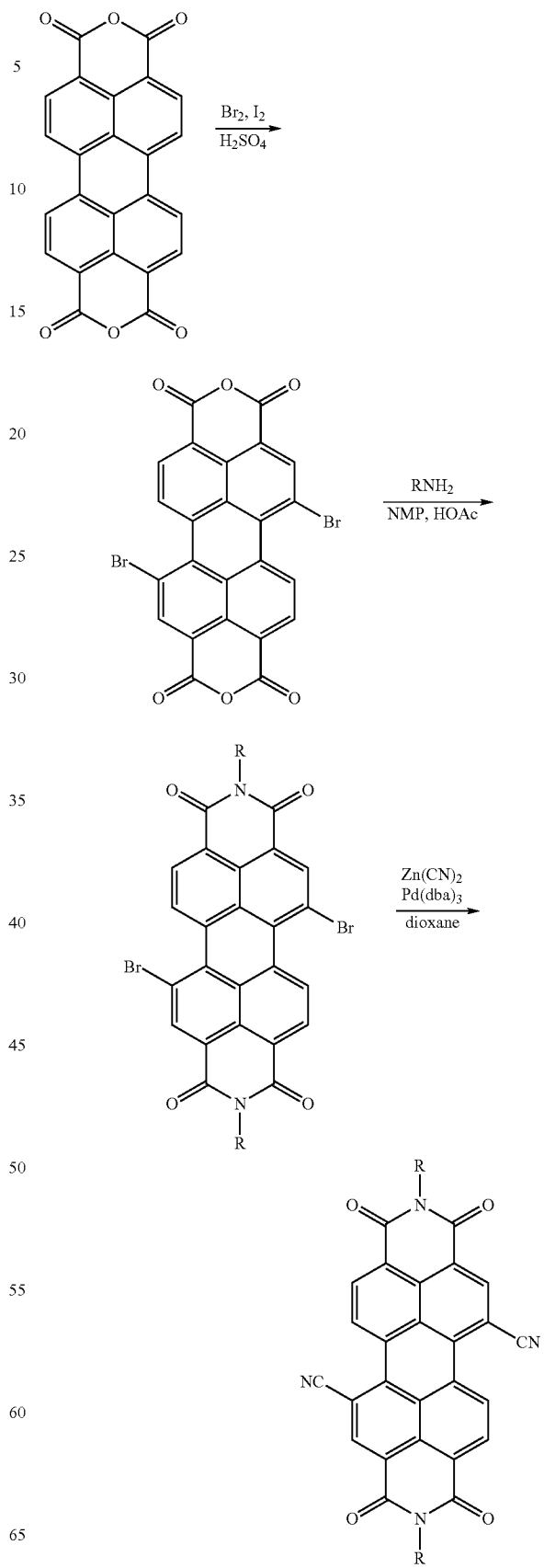

Example 7

Vapor-deposited OFETs in the top-contact configuration were fabricated in the following manner. Films of PDI-FCN$_2$ and PDI-CN$_2$ ~50 nm thick were vapor deposited (0.2 Å s$^{-1}$, P~10$^{-6}$ Torr) onto a n$^+$-doped Si (100) wafer with a 300 nm thermally grown SiO$_2$ dielectric layer. Gold electrodes 40 nm thick were thermally evaporated onto the thin films through a shadow mask. Silicon substrates were treated with 1,1,1,3,3,3-hexamethyldisilazane vapor prior to film deposition. Substrate temperature during film deposition was varied with a cartridge heater.

Bottom contact devices were fabricated by evaporating 40 nm thick gold electrodes directly onto the HMDS treated silicon substrate followed by deposition of the organic film under the same conditions as above. Alkane thiol treatment of the gold electrodes was accomplished by submerging the substrate in a 10$^{-3}$ M ethanol solution of octadecanethiol for 3 hours. The substrates were then rinsed with ethanol and dried prior to film deposition.

Figure 14:
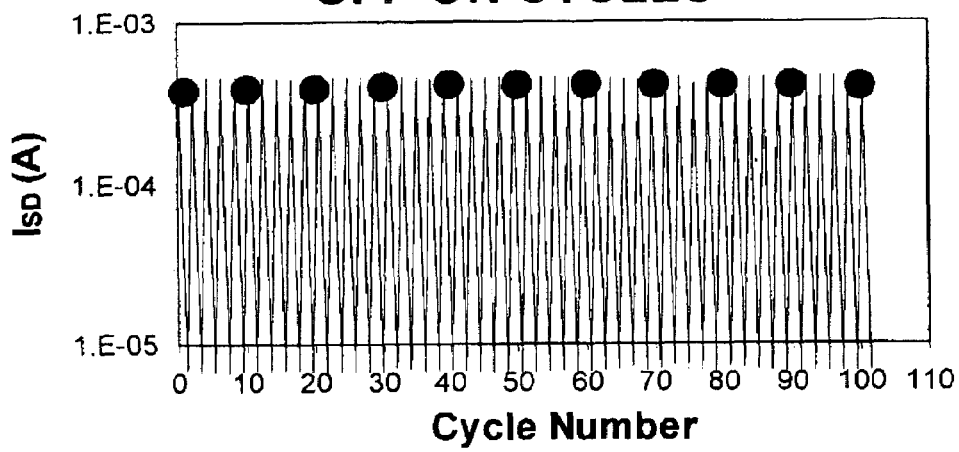
FIG. 14. A graphic representation of the longevity and stability available from an OFET comprising a PDI-FCN2 thin film, showing minimal change in mobilities during cycling.
Figure 15:
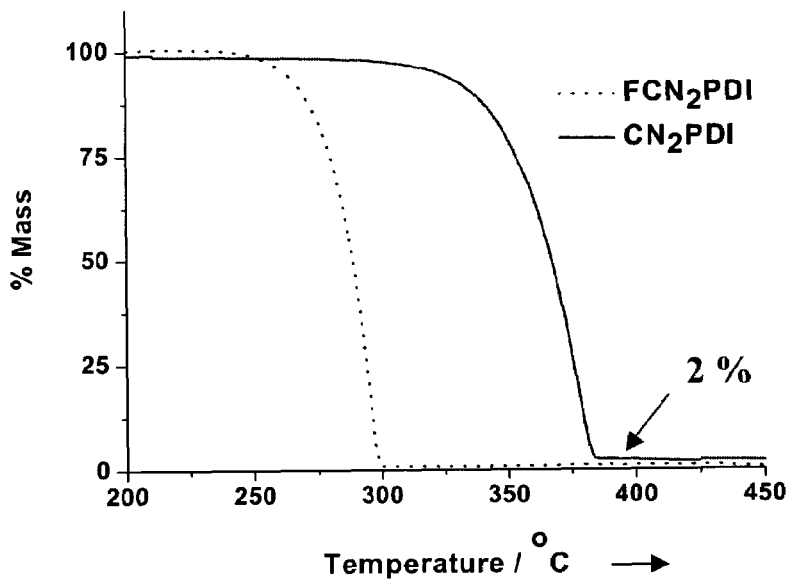
FIG. 15. TGA scan of $FCN_2$ PDI and $CN_2PDI$ at 2 Torr. The temperature ramp rate is 1.5° C./min.
Figure 16:
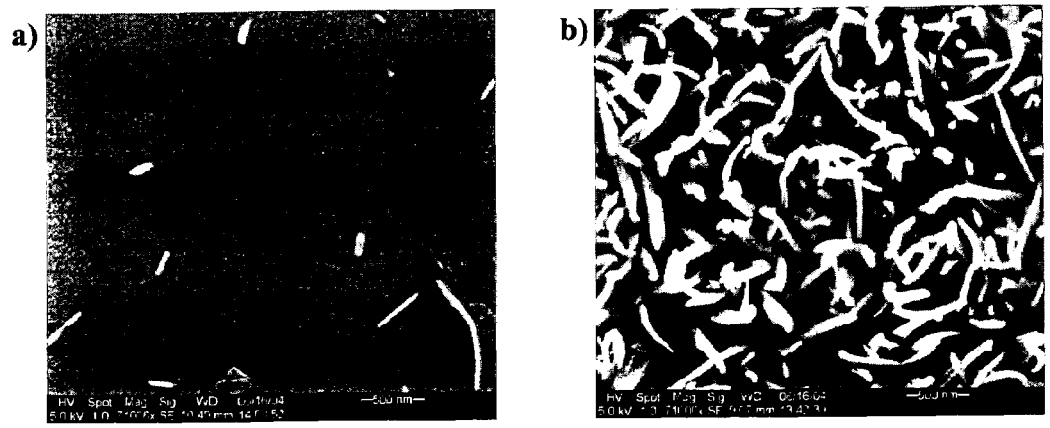
FIG. 16. SEM micrographs of 50 mm thick films of a) $PDI-FCN_2$ deposited on a 1° C. HMDS-treated Si(100) substrate and b) $PDI-CN_2$ deposited on a 90° C. HMDS-treated Si(100) substrate.
Figure 17:
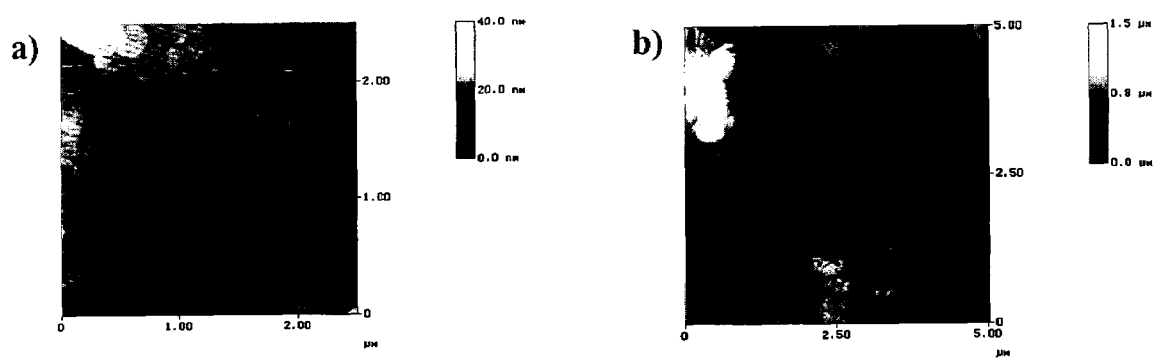
FIG. 17. Tapping mode AFM images of a) $PDI-FCN_2$ deposited on Si(100) at 110° C. and b) $PDI-CN_2$ deposited on Si(100) at 90° C.
Figure 18:
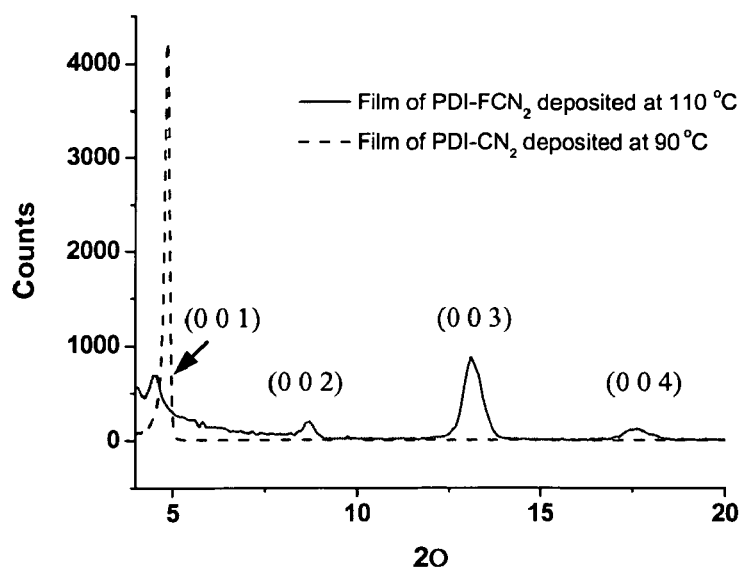
FIG. 18. Thin film Θ-2Θ X-ray diffraction from $PDI-FCN_2$ and $PDI-CN_2$ films deposited on Si(100) at 110° C. and 90° C., respectively. Reflections are assigned for $PDI-FCN_2$ from the single crystal diffraction data.

Solution-cast films were fabricated by drip-casting. First, the outer edge of the substrate was coated with Novec-ECC 1700 electronic coating to define an area for solution containment. The substrate was heated to 90° C., and ~1 mL of a 10$^{-3}$ M solution of the material was deposited. During the slow evaporation process, the substrates were protected from atmospheric currents by containment in a glass vessel. Films of PDI-FCN$_2$ were cast from toluene, while films of PDI-CN$_2$ were cast from chloroform. A device comprising PDI-FCN$_2$ was operated in ambient for over 100 cycles with minimal change in device behavior (see, FIG. 14).

Example 8

TGA, SEM, AFM and XRD results for PDI-CN$_2$ and PDI-FCN$_2$ films are provided in FIGS. 15-18, respectively.

Example 9 synthesis of N,N'-bis(n-octyl)-(1,7 & 1,6)-dicyanoperylene-3,4:9,10-bis(dicarboximide), PDI-8CN$_2$. N,N'-bis(n-octyl)-(1,7 & 1,6)-dibromoperylene-3,4:9,10-bis(dicarboximide) (1.318 g, 1.71 mmol) and copper (I) cyanide (1.550 g, 17.31 mmol) were combined in a 50 ml round bottom flask with 20 ml dry DMF. This mixture was placed in a sonication bath for 30 minutes then heated to 130° C. under a nitrogen atmosphere for 5 hours. The DMF was then removed under reduced pressure leaving a reddish/brown residue behind. Soxhlet extraction with chloroform for 36 hours provided the title compound as a red powder in 69% yield, (0.777 g, 1.17 mmol). Mass spectrum (m/z) 663.10 (calc. 664.30) $^1$H NMR (CDCl$_3$) Integrations reported are for the 1,7 isomer (~90% pure) ([] indicates 1,6 or 1,7-isomer): δ 9.700 (d, J=8.2 Hz, [1.7 (1,6 unresolvable)] 2H), 9.023 (s, [1,6]), 8.972 (s, [1,7], 2H), 8.924 (d, J=8.2 Hz, [1,7], 2H), 8.863 (d, J=8.2 Hz, [1,6]), 4.219 (m, 4H), 1.763 (m, 4H), 1.45-1.20 (m, 20H), 0.884 (t, J=6.7 Hz, 6H). (The dicarboximide was prepared according to Ulrike, et al., *J. Matt. Chem.* (2001), 11(7), 1789-1799).

Example 10 the electronic properties of PDI-8CN$_2$ (N-octyl) are virtually indistinguishable from that of PDI-CN$_2$ (N-cyclohexyl), with an absorption maximum at 530 nm, emission maximum at 547 nm, and first reduction potential of −0.1 vs. S.C.E. placing the HOMO at ~6.6 eV and the LUMO at ~4.3 eV vs. vacuum level. The reduced pressure (5 Torr) TGA of PDI-8CN$_2$ reveals that the material evaporates with less than 10% decomposition at ~325° C. Simultaneously acquired DTA data reveals a solid-liquid transition prior to evaporation at ~300° C.

Example 11

Films of PDI-8Cn$_2$ were deposited from the vapor phase onto analogous substrates as used in the studies on PDI-CN$_2$ and PDI-FCN$_2$. Gold electrodes in the top-contact configuration were also deposited in the same manner as before.

Example 12

Transistors were characterized as before. At substrate temperatures during deposition of >90° C., mobilities as high as 0.2 cm$^2$ V$^{-1}$ s$^{-1}$ are observed. The devices have threshold voltages of ~−6 V and I$_{ON}$/I$_{OFF}$ ratios as high as 10$^4$. (See

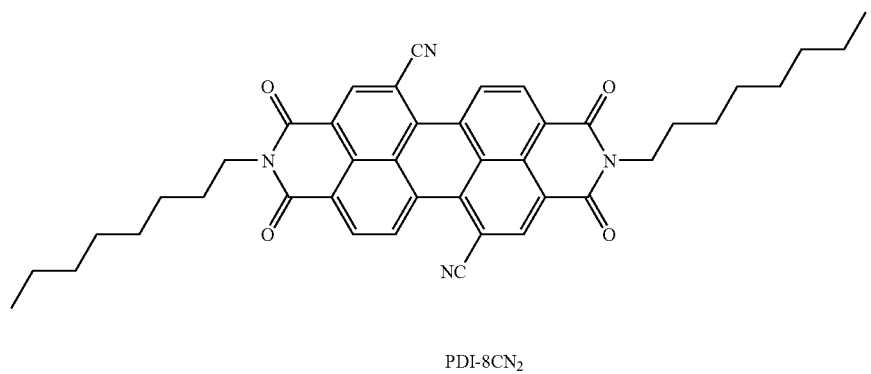

PDI-8CN$_2$

Figure 19:
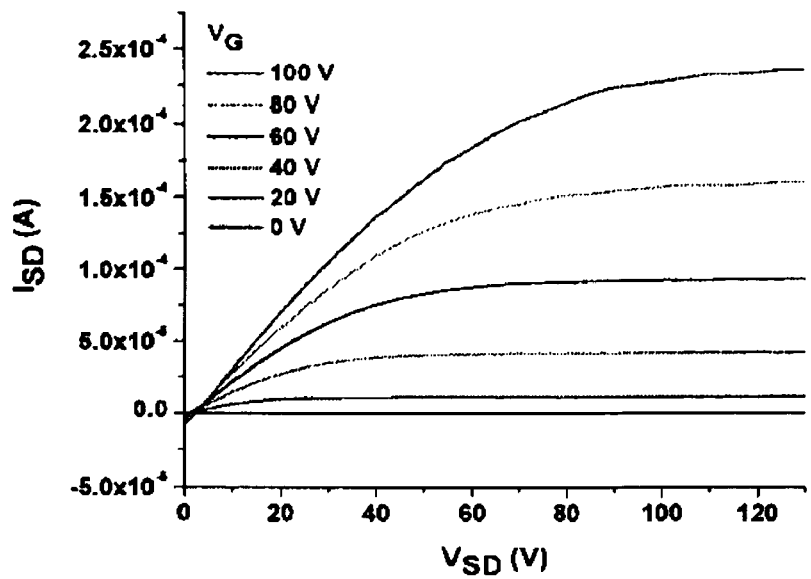
FIG. 19: I-V Curve for an organic transistor comprising a semiconductor film of PDI-8CN$_2$ deposited at 130° C.

FIG. 19.) These device also operate under both inert and ambient atmosphere with negligible differences.

Example 13

With reference to Table 3, below, this example further illustrates perylene compounds, materials and/or films of the type available through this invention. Such compounds can comprise any moiety R$^9$ and/or R$^{10}$ in combination with at least one of the substituents and moieties for any one or more of $R^1$-$R^{10}$, $R^{11}$, and $R^{12}$. Such N- and core-substituted compounds are available through the synthetic techniques described herein or straight modifications thereof as would be understood by those skilled in the art. With reference to example 6, preparation of a desired imide is limited only by choice of amine reagent and the corresponding mono- or dianhydride starting material. For instance, $R^9$ and/or $R^{10}$ can be an alkyl (substituted or unsubstituted) or polyether moiety through use of the respective amino-terminated alkyl reagent or ethylene glycol oligomer. Likewise, various core substituents can be introduced by chemistry on commercially-available perylene anhydrides or bromo-substituted analogs thereof, using variations of aromatic acylation, alkylation and/or substitution reactions known in the art (e.g., Cu-catalyzed fluoroalkyl substitution reactions described in U.S. Pat. No. 6,585,914, the entirety of which is incorporated herein by reference). In an analogous manner, a comparable range of N- and core-substituted naphthalene compounds are available from the corresponding starting materials and reagents.

TABLE 3

| $R_9$ |
|---|
| H, $(CH_2)_2CF_3$, $C_5HF_8$, |
| $C_6F_5$, $C_8H_2F_{15}$, |
| $C_6H_4X$; (X = H, Cl, F, $^+N(CH_3)_3$), |
| $C_{16}H_{31}F_3$, any of $R^{10}$ |

| $R^{10}$ |
|---|
| Any of $R^9$, $C_6H_9F_2$ |
| $C_5H_{12}$, $C_8H_{14}F_3$, |
| $C_6H_4X$; X = H, CN, $NO_2$ |
| $(CH_2CH_2O)_nC_2H_4OH$; n = 1-7 |

| $R^1$-$R^8$, $R^{11}$, and $R^{12}$ |
|---|
| H, CN, $NO_2$, halide, $SO_3H$, |
| $^+N(R)_3$; (R = H, alkyl), $CH_2CF_3$, |
| C(O)R; (R = H, alkyl, phenyl), |
| $CO_2R$; (R = H, alkyl, phenyl), |
| $C_6H_4X$; (X = H, F, CN, $NO_2$) |

We claim:

1. An n-type semiconductor compound having formula I:

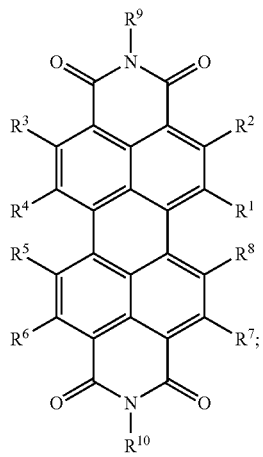

wherein:
each of $R^1$-$R^8$ independently is selected from H, $-NO_2$, $-CN$, halide, $-SO_3H$, $-N^+H_3$, $-N^+H_2$(alkyl), $-N^+H$(alkyl)$_2$, $-N^+$(alkyl)$_3$, $-C(O)R$, $-CO_2R$, an alkyl moiety, a substituted alkyl moiety, a cycloalkyl moiety, a substituted cycloalkyl moiety, an aryl moiety, a substituted aryl moiety, a polycyclic aryl moiety, and a substituted polycyclic aryl moiety,
  wherein each of the alkyl moiety, the substituted alkyl moiety, the cycloalkyl moiety, the substituted cycloalkyl moiety, the aryl moiety, the substituted aryl moiety, the polycyclic aryl moiety, and the substituted polycyclic aryl moiety comprises at least one of $-NO_2$, $-CN$, halide, $-SO_3H$, $-N^+H_3$, $-N^+H_2$(alkyl), $-N^+H$(alkyl)$_2$, $-N^+$(alkyl)$_3$, $-C(O)R$, and $-CO_2R$, and
at least one of $R^1$, $R^4$, $R^5$, and $R^8$ is $-CN$;
$R^9$ and $R^{10}$ independently are selected from H, an alkyl moiety, a substituted alkyl moiety, a cycloalkyl moiety, a substituted cycloalkyl moiety, an aryl moiety, and a substituted aryl moiety,
  wherein each of the alkyl moiety, the substituted alkyl moiety, the cycloalkyl moiety, the substituted cycloalkyl moiety, the aryl moiety, and the substituted aryl moiety optionally comprises $-NO_2$, $-CN$, halide, $-SO_3H$, $-N^+H_3$, $-N^+H_2$(alkyl), $-N^+H$(alkyl)$_2$, $-N^+$(alkyl)$_3$, $-C(O)R$, or $-CO_2R$,
  each methylene ($-CH_2-$) in the alkyl moiety or the substituted alkyl moiety optionally is replaced with a heteroatom selected from O and N, and
  each methene ($-CH=$) in the aryl moiety or the substituted aryl moiety optionally is replaced with a heteroatom selected from O and N; and
R, at each occurrence, is H, an alkyl moiety, or phenyl.

2. The compound of claim 1, wherein at least one of $R^9$ and $R^{10}$ is selected from an alkyl moiety, a substituted alkyl moiety, and a cycloalkyl moiety.

3. The compound of claim 2, wherein at least one of $R^9$ and $R^{10}$ is a halo substituted alkyl moiety.

4. The compound of claim 3, wherein the halo substituted alkyl moiety comprises F or Cl.

5. The compound of claim 1, wherein each of $R^1$ and $R^4$ or each of $R^5$ and $R^8$ is $-CN$.

6. The compound of claim 5, wherein each of $R^2$, $R^3$, $R^6$, and $R^7$ is H, whichever of $R^1$, $R^4$, $R^5$, and $R^8$ that is not —CN is H, and $R^9$ and $R^{10}$ independently are an alkyl moiety, a substituted alkyl moiety, or a cycloalkyl moiety.

7. The compound of claim 1, wherein each of $R^1$ and $R^5$ or each of $R^4$ and $R^8$ is —CN.

8. The compound of claim 7, wherein each of $R^2$, $R^3$, $R^6$, and $R^7$ is H, whichever of $R^1$, $R^4$, $R^5$, and $R^8$ that is not —CN is H, and $R^9$ and $R^{10}$ independently are an alkyl moiety, a substituted alkyl moiety, or a cycloalkyl moiety.

9. The compound of claim 1, wherein each of $R^1$, $R^4$, $R^5$, and $R^8$ is —CN.

10. An n-type semiconductor compound selected from:
N,N'-bis(cyclohexyl)-1,7-dicyano-perylene-3,4:9,10-bis(dicarboximide);
N,N'-bis(cyclohexyl)-1,6-dicyano-perylene-3,4:9,10-bis(dicarboximide);
N,N'-bis(1H,1H-perfluorobutyl)-1,7-dicyano-perylene-3,4:9,10-bis(dicarboximide);
N,N'-bis(1H,1H-perfluorobutyl)-1,6-dicyano-perylene-3,4:9,10-bis(dicarboximide);
N,N'-bis(n-octyl)-1,7-dicyano-perylene-3,4:9,10-bis(dicarboximide);
N,N'-bis(n-octyl)-1,6-dicyano-perylene-3,4:9,10-bis(dicarboximide);
N,N'-bis(n-octyl)-1-cyano-7-bromo-perylene-3,4:9,10-bis(dicarboximide); and
N,N'-bis(n-octyl)-1-cyano-6-bromo-perylene-3,4:9,10-bis(dicarboximide).

11. An n-type semiconductor compound having formula III:

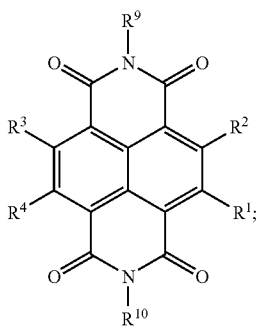

wherein:
two of $R^1$-$R^4$ are —CN and the other two of $R^1$-$R^4$ are H;
$R^9$ and $R^{10}$ independently are selected from H, an alkyl moiety, a substituted alkyl moiety, a cycloalkyl moiety, a substituted cycloalkyl moiety, an aryl moiety, and a aryl moiety, wherein at least one of $R^9$ and $R^{10}$ is a halo substituted alkyl moiety,
  wherein each of the alkyl moiety, the substituted alkyl moiety, the cycloalkyl moiety, the substituted cycloalkyl moiety, the aryl moiety, and the substituted aryl moiety optionally comprises —$NO_2$, —CN, halide, —$SO_3H$, —$N^+H_3$, —$N^+H_2$(alkyl), —$N^+H$(alkyl)$_2$, —$N^+$(alkyl)$_3$, —C(O)R, or —$CO_2R$,
  each methylene (—$CH_2$—) in the alkyl moiety or the substituted alkyl moiety optionally is replaced with a heteroatom selected from O and N, and
  each methene (—CH=) in the aryl moiety or the substituted aryl moiety optionally is replaced with a heteroatom selected from O and N; and R, at each occurrence, is H, an alkyl moiety, or phenyl.

12. The compound of claim 11, wherein each of $R^1$ and $R^4$ or each of $R^2$ and $R^3$ is —CN.

13. The compound of claim 11, wherein each of $R^1$ and $R^3$ or each of $R^2$ and $R^4$ is —CN.

14. A composite comprising a substrate and a semiconductor component thereon, said semiconductor component comprising a compound of formula I':

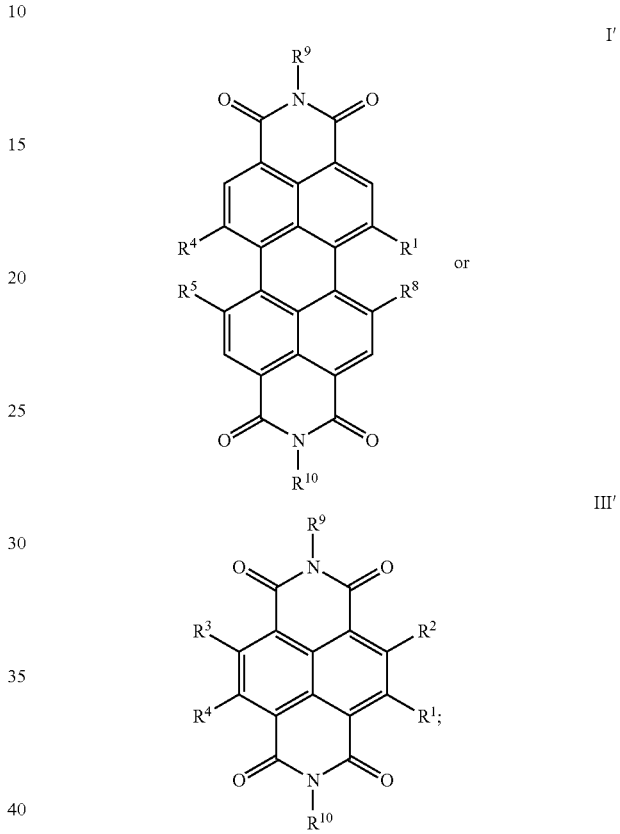

wherein:
$R^1$, $R^4$, $R^5$, and $R^8$ independently are selected from H and —CN,
  wherein at least one of $R^1$, $R^4$, $R^5$, and $R^8$ is —CN;
$R^9$ and $R^{10}$ independently are selected from H, an alkyl moiety, a substituted alkyl moiety, a cycloalkyl moiety, a substituted cycloalkyl moiety, an aryl moiety, and a substituted aryl moiety,
  wherein each of the alkyl moiety, the substituted alkyl moiety, the cycloalkyl moiety, the substituted cycloalkyl moiety, the aryl moiety, and the substituted aryl moiety optionally comprises —$NO_2$, —CN, halide, —$SO_3H$, —$N^+H_3$, —$N^+H_2$(alkyl), —$N^+H$(alkyl)$_2$, —$N^+$(alkyl)$_3$, —C(O)R, or —$CO_2R$,
  each methylene (—$CH_2$—) in the alkyl moiety or the substituted alkyl moiety optionally is replaced with a heteroatom selected from O and N, and
  each methene (—CH=) in the aryl moiety or the substituted aryl moiety optionally is replaced with a heteroatom selected from O and N; and
R, at each occurrence, is H, an alkyl moiety, or phenyl.

15. The composite of claim 14, wherein $R^9$ and $R^{10}$ independently are selected from an alkyl moiety, a substituted alkyl moiety, a cycloalkyl moiety, and a substituted aryl moiety.

16. The composite of claim 15, wherein at least one of $R^9$ and $R^{10}$ is a halo substituted alkyl moiety.

17. The composite of claim 16, wherein the halo substituted alkyl moiety comprises F or Cl.

18. The composite of claim 14, wherein each of $R^1$ and $R^4$ or each of $R^5$ and $R^8$ is —CN.

19. The composite of claim 18, wherein $R^9$ and $R^{10}$ independently are an alkyl moiety, a substituted alkyl moiety, or a cycloalkyl moiety.

20. The composite of claim 14, wherein each of $R^1$ and $R^5$ or each of $R^4$ and $R^8$ is —CN.

21. The composite of claim 20, wherein, $R^9$ and $R^{10}$ independently are an alkyl moiety, a substituted alkyl moiety, or a cycloalkyl moiety.

22. The composite of claim 14, wherein the compound is selected from:
N,N'-bis(cyclohexyl)-1,7-dicyano-perylene-3,4:9,10-bis(dicarboximide);
N,N'-bis(cyclohexyl)-1,6-dicyano-perylene-3,4:9,10-bis(dicarboximide);
N,N'-bis(1H,1H-perfluorobutyl)-1,7-dicyano-perylene-3,4:9,10-bis(dicarboximide);
N,N'-bis(1H,1H-perfluorobutyl)-1,6-dicyano-perylene-3,4:9,10-bis(dicarboximide);
N,N'-bis(n-octyl)-1,7-dicyano-perylene-3,4:9,10-bis(dicarboximide);
N,N'-bis(n-octyl)-1,6-dicyano-perylene-3,4:9,10-bis(dicarboximide);
N,N'-bis(n-octyl)-1-cyano-7-bromo-perylene-3,4:9,10-bis(dicarboximide); and
N,N'-bis(n-octyl)-1-cyano-6-bromo-perylene-3,4:9,10-bis(dicarboximide).

23. The composite of claim 14, wherein the composite is incorporated into an OFET device.

24. An n-type semiconductor compound selected from:
N,N'-bis(cyclohexyl)-1,7-dicyano-perylene-3,4:9,10-bis(dicarboximide); and
N,N'-bis(cyclohexyl)-1,6-dicyano-perylene-3,4:9,10-bis(dicarboximide).

25. An n-type semiconductor compound selected from:
N,N'-bis(1H,1H-perfluorobutyl)-1,7-dicyano-perylene-3,4:9,10-bis(dicarboximide); and
N,N'-bis(1H,1H-perfluorobutyl)-1,6-dicyano-perylene-3,4:9,10-bis(dicarboximide).

26. An n-type semiconductor compound selected from:
N,N'-bis(n-octyl)-1,7-dicyano-perylene-3,4:9,10-bis(dicarboximide); and
N,N'-bis(n-octyl)-1,6-dicyano-perylene-3,4:9,10-bis(dicarboximide).

27. A composite comprising a substrate and a semiconductor component thereon, said semiconductor component comprising a compound of formula III':

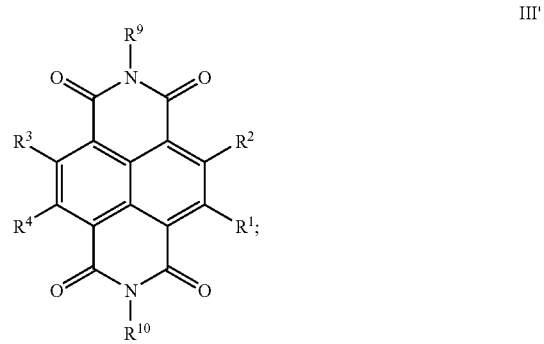

wherein:
$R^1$, $R^2$, $R^3$, and $R^4$ independently are selected from H and —CN, wherein two of $R^1$-$R^4$ are —CN and the other two of $R^1$-$R^4$ are H;

$R^9$ and $R^{10}$ independently are selected from H, an alkyl moiety, a substituted alkyl moiety, a cycloalkyl moiety, a substituted cycloalkyl moiety, an aryl moiety, and a substituted aryl moiety, wherein at least one of $R^9$ and $R^{10}$ independently is a halo substituted alkyl moiety, wherein each of the alkyl moiety, the substituted alkyl moiety, the cycloalkyl moiety, the substituted cycloalkyl moiety, the aryl moiety, and the substituted aryl moiety optionally comprises —$NO_2$, —CN, halide, —$SO_3H$, —$N^+H_3$, —$N^+H_2$(alkyl), —$N^+H$(alkyl)$_2$, —$N^+$(alkyl)$_3$, —C(O)R, or —$CO_2R$, each methylene (—$CH_2$=) in the alkyl moiety or the substituted alkyl moiety optionally is replaced with a heteroatom selected from O and N, and each methene (—CH=) in the aryl moiety or the substituted aryl moiety optionally is replaced with a heteroatom selected from O and N; and R, at each occurrence, is H, an alkyl moiety, or phenyl.

28. The composite of claim 27, wherein the halo substituted alkyl moiety comprises F or Cl.

29. The compound of claim 11, wherein the halo substituted alkyl moiety comprises F or Cl.

\* \* \* \* \*

UNITED STATES PATENT AND TRADEMARK OFFICE
CERTIFICATE OF CORRECTION

PATENT NO. : 7,671,202 B2  Page 1 of 1
APPLICATION NO. : 11/043814
DATED : March 2, 2010
INVENTOR(S) : Marks et al.

It is certified that error appears in the above-identified patent and that said Letters Patent is hereby corrected as shown below:

In claim 11, at column 21, lines 53-54, please delete "a aryl moiety, wherein" and replace with --a substituted aryl moiety, wherein--.

In claim 14, at column 22, lines 20-40, please delete "or

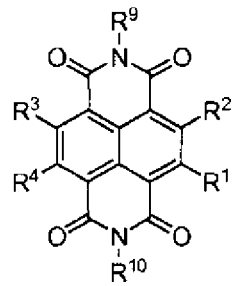

III' ".

In claim 27, at column 24, line 36, please delete "($-CH_2=$)" and replace with --($-CH_2-$)--.

Signed and Sealed this

Twenty-eighth Day of September, 2010

David J. Kappos
*Director of the United States Patent and Trademark Office*